(12) United States Patent
Nielsen et al.

(10) Patent No.: US 8,703,048 B2
(45) Date of Patent: Apr. 22, 2014

(54) BUFFERED SWELLING MEDIA FOR RADIATION STERILIZED HYDROPHILIC COATINGS

(75) Inventors: Bo Rud Nielsen, Alleroed (DK); Niels Joergen Madsen, Alleroed (DK)

(73) Assignee: Coloplast A/S, Humlebaek (DK)

( * ) Notice: Subject to any disclaimer, the term of this patent is extended or adjusted under 35 U.S.C. 154(b) by 584 days.

(21) Appl. No.: 12/737,116

(22) PCT Filed: Jun. 16, 2009

(86) PCT No.: PCT/DK2009/050130
§ 371 (c)(1),
(2), (4) Date: Dec. 9, 2010

(87) PCT Pub. No.: WO2010/003419
PCT Pub. Date: Jan. 14, 2010

(65) Prior Publication Data
US 2011/0106061 A1    May 5, 2011

(30) Foreign Application Priority Data

Jun. 16, 2008 (DK) .................................. 2008 00834
Sep. 9, 2008 (DK) .................................. 2008 01262

(51) Int. Cl.
*A61L 2/00* (2006.01)
(52) U.S. Cl.
USPC ......................................................... 422/23
(58) Field of Classification Search
USPC ............................................ 604/544; 422/23
See application file for complete search history.

(56) References Cited

U.S. PATENT DOCUMENTS

| | | | |
|---|---|---|---|
| 3,967,728 | A | 7/1976 | Gordon et al. |
| 4,100,309 | A | 7/1978 | Micklus et al. |
| 4,119,094 | A | 10/1978 | Micklus et al. |
| 4,373,009 | A | 2/1983 | Winn |
| 4,437,567 | A | 3/1984 | Jeng |
| 4,459,317 | A | 7/1984 | Lambert |
| 4,477,438 | A | 10/1984 | Willcockson et al. |

(Continued)

FOREIGN PATENT DOCUMENTS

| | | |
|---|---|---|
| CN | 1031650 | 3/1989 |
| DE | 41 42 319 | 6/1993 |

(Continued)

OTHER PUBLICATIONS

Niels Linnet: "pH measurements in theory and practice", 1.ed., Radiometer A/S, Copenhagen, 1970.

(Continued)

*Primary Examiner* — Nicholas Lucchesi
*Assistant Examiner* — Diva K Chander
(74) *Attorney, Agent, or Firm* — Coloplast Corp., Coloplast A/S; Nick Baumann

(57) ABSTRACT

To identify an alternative swelling medium with a hydrophilic polymer, we have observed that a swelling medium containing only 6% PEG 2000 and 0.9% NaCl failed to protect a hydrophilic coating during electron beam sterilization and subsequent storage at ambient and higher temperatures in an accelerated storage stability test. An unacceptably low dry-out time, below the specified 5 minutes, was obtained. However, when the biological buffer sodium citrate was added to a swelling medium containing PEG 2000, the performance of the stored catheters was as good as or better than the performance of catheters stored with the conventional swelling medium.

20 Claims, 33 Drawing Sheets

(56) References Cited

U.S. PATENT DOCUMENTS

Figure 1:
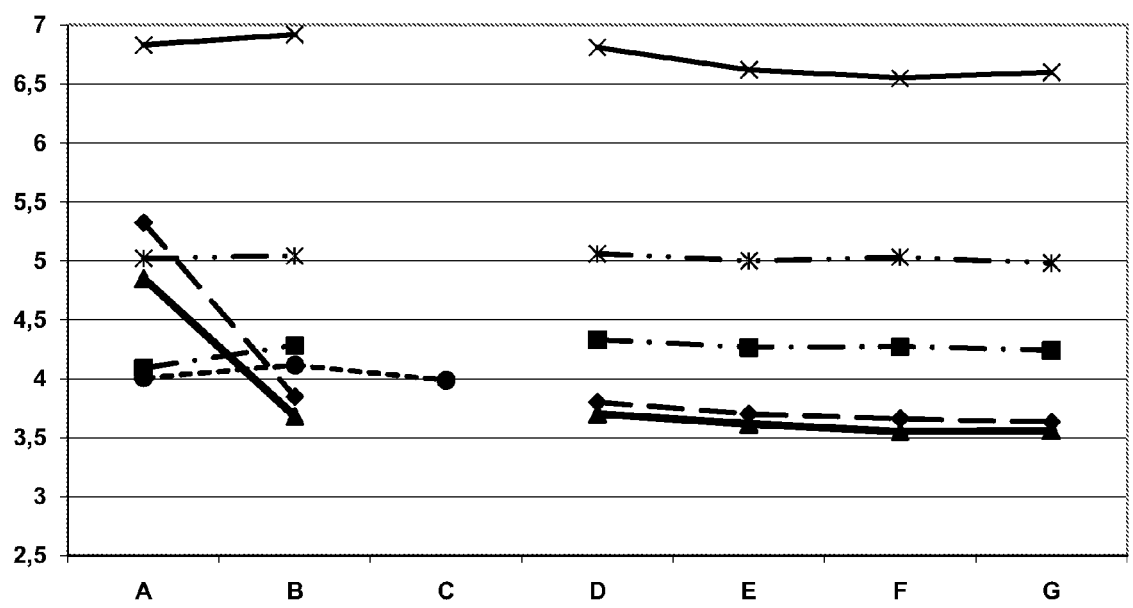

| Patent No. | | Date | Inventor |
|---|---|---|---|
| 4,515,593 | A | 5/1985 | Norton |
| 4,754,877 | A | 7/1988 | Johansson et al. |
| 4,792,914 | A | 12/1988 | Dartois et al. |
| 4,889,689 | A | 12/1989 | Tsao |
| 4,895,566 | A * | 1/1990 | Lee ............................. 604/266 |
| 4,917,686 | A | 4/1990 | Bayston et al. |
| 5,008,106 | A | 4/1991 | Merianos et al. |
| 5,041,100 | A | 8/1991 | Rowland et al. |
| 5,120,816 | A | 6/1992 | Gould et al. |
| 5,130,124 | A | 7/1992 | Merianos et al. |
| 5,296,583 | A | 3/1994 | Levy |
| 5,312,619 | A | 5/1994 | Shih et al. |
| 5,357,636 | A | 10/1994 | Dresdner et al. |
| 5,589,507 | A | 12/1996 | Hall, II et al. |
| 5,882,526 | A | 3/1999 | Brown et al. |
| 5,951,458 | A | 9/1999 | Hastings et al. |
| 6,203,536 | B1 | 3/2001 | Berg et al. |
| 6,617,291 | B1 | 9/2003 | Smith |
| 6,986,868 | B2 * | 1/2006 | Madsen ........................ 422/23 |
| 7,833,475 | B2 * | 11/2010 | Madsen ........................ 422/23 |
| 8,487,284 | B2 * | 7/2013 | Tateshima et al. ........ 250/504 R |
| 2001/0001443 | A1 | 5/2001 | Kayerod et al. |
| 2002/0037943 | A1 | 3/2002 | Madsen |
| 2002/0120333 | A1 | 8/2002 | Keogh et al. |
| 2002/0192297 | A1 | 12/2002 | Ramirez et al. |
| 2003/0065292 | A1 | 4/2003 | Darouiche et al. |
| 2005/0214443 | A1 | 9/2005 | Madsen |
| 2011/0106061 | A1 * | 5/2011 | Nielsen et al. ................. 604/544 |

FOREIGN PATENT DOCUMENTS

| | | |
|---|---|---|
| DK | 159018 B | 8/1990 |
| EP | 0 093 093 A1 | 11/1983 |
| EP | 0 217 771 | 4/1987 |
| EP | 0 265 381 | 4/1988 |
| EP | 0 306 212 | 3/1989 |
| EP | 0 379 156 | 7/1990 |
| EP | 0 389 632 | 10/1990 |
| EP | 0 454 293 | 10/1991 |
| EP | 1 131 112 | 9/2001 |
| EP | 1 252 898 A2 | 10/2002 |
| GB | 1 500 707 | 2/1978 |
| GB | 1 600 963 | 10/1981 |
| JP | 55-12265 | 3/1980 |
| JP | 58-118765 | 7/1983 |
| JP | 2001-511659 | 8/2001 |
| JP | 2004-500414 | 1/2004 |
| WO | WO 86/06284 | 11/1986 |
| WO | WO 89/04674 | 6/1989 |
| WO | WO 90/05162 | 5/1990 |
| WO | WO 91/09807 | 7/1991 |
| WO | WO 91/19756 A1 | 12/1991 |
| WO | WO 94/16747 A1 | 8/1994 |
| WO | WO 97/42901 | 11/1997 |
| WO | WO 98/11932 | 3/1998 |
| WO | WO 99/65538 | 12/1999 |
| WO | WO 00/30696 | 6/2000 |
| WO | WO 00/30696 A1 | 6/2000 |
| WO | WO 00/47494 | 8/2000 |
| WO | WO 01/43807 | 6/2001 |
| WO | WO 01/74765 | 10/2001 |
| WO | WO 02/26277 | 4/2002 |
| WO | WO 02/100455 | 12/2002 |
| WO | WO 2006/117372 A1 | 11/2006 |

OTHER PUBLICATIONS

Encyclopedia of Polymer Science and Engineering, eds. H.F. Mark; N.M. Bikales, C.G. Overberger, and G. Menges, 2. ed., vol. 13, pp. 292-4, Wiley-Interscience, New York, 1988.

De Kimpe et al. "Reactive Oxygen Species Regulate Macrophage Scavenger Receptor Type I, but Not Type II, in the Human Monocytic Cell Line THP-1." Molecular Pharmacology, vol. 53, 1998, p. 1076-1082.

Kuczynski et al. "DTPMPA: polyamino polyphosphonic acid and its use in paper processes." Tappi Journal, vol. 71(6), 1998, pp. 171-174.

Xu et al. "$H_2O_2$ Bleaching of Mechanical Pulps. Part IV: $H_2O_2$ Consumption." Journal of Pulp and Paper Science, vol. 28(11), 2002, pp. 379-383.

Jaschinski et al "Use of high temperature resistant chelants in peroxide bleaching of kraft pulps." Pulp and Paper Canada, vol. 99(8), 1998, pp. 52-55.

Kassem et al. "Further investigation on the effect of iron as a catalyst on the stability of hydrogen peroxide solution and its action in presence of different stabilizer." Bulletin of Faculty of Pharmacy, Cairo University, vol. 10(1), 1971, pp. 265-273.

Nerst et al. "Uber das Stabilitatsgebiet des Wasserstoffsuperoxyds" Zeitschrift fur physikalische Chemie, Stochiometrie under Verwandtschaftslehre vol. 46, 1903, pp. 720-724.

* cited by examiner

BUFFERED SWELLING MEDIA FOR RADIATION STERILIZED HYDROPHILIC COATINGS

This is a national stage of PCT/DK09/050,130 filed Jun. 16, 2009 and published in English, which has a priority of Denmark no. PA 2008 00834 filed Jun. 16, 2008, and Denmark no. PA 2008 01262 filed Sep. 9, 2008, hereby incorporated by reference.

BACKGROUND

It is known to coat medical devices, e.g. catheters for introduction into human cavities, such as blood vessels, digestive organs and the urinary system, with a hydrophilic coating, normally as a minimum applied on that part of the surface which is introduced or comes into contact with mucous membranes, etc., during introduction of the device. Whereas such a coating is not particularly slippery when dry it becomes extremely slippery when it is swelled with water, preferably immediately before introduction into the human body. The hydrophilic coating thus ensures a substantially painless introduction with a minimum of damage on tissue.

U.S. Pat. No. 3,967,728 to Gordon discloses the use of a sterile lubricant for deposition on and lubricating an uncoated catheter before use.

WO 86/06284 (Astra Meditech Aktiebolag) discloses a wetting and storing device for a coated catheter in which the coating may be wetted using water or water comprising common salt and possibly bactericidal compounds or other additives.

WO 94/16747 discloses a hydrophilic coating with improved retention of water on a surface, especially a surface of a medical device such as a urethra catheter, prepared by applying to the surface in one or more process steps at least one solution of components that will combine to form the hydrophilic coating. During the final step the surface is coated with an osmolality promoting agent, which is dissolved or emulsified in the solution or in the last solution to be applied when forming the hydrophilic coating.

Most prior art coatings are developed for instant swelling immediately before use of the medical device on which the coatings are applied.

It has been found, however, that most hydrophilic coatings lose their water retention and that the coefficient of friction increases when the coatings are stored in water for an extended period of time, particularly after sterilisation using irradiation or autoclaving.

It is described in EP 1 131 112 that the water retention can be increased dramatically and the initial coefficient of friction can be kept low by carrying out sterilisation of a medical device having a hydrophilic coating while in contact with an aqueous solution comprising hydrophilic polymers, for example polyvinylpyrrolidone or copolymers containing N-vinylpyrrolidone; poly[(meth)acrylic acid] or copolymers containing (meth)acrylic acid or (meth)acrylic acid esters; polyacrylamides; poly(vinyl alcohol) and copolymers of partially saponified vinyl acetate copolymers; poly(ethylene glycol); poly(vinyl methyl ether) or copolymers containing vinyl methyl ether, such as poly(vinyl methyl ether-co-maleic anhydride); copolymers containing maleic anhydride or maleic acid esters; or water soluble polysaccharides or derivatives thereof, such as carboxymethylcellulose (CMC) or hydroxyethylcellulose or xanthane or a derivative thereof. Thus, it seems that the hydrophilic polymers protect the above-mentioned properties during exposure to sterilisation using radiation when wetted with such a polymer solution.

However, there is still a need for methods for providing a sterilised medical device with a hydrophilic coating. Also there is a need for new ways of providing the hydrophilic polymer in a sufficient amount in the aqueous wetting liquid for the sterilisation to be carried out without detrimental effect to the water retention and the initial friction of the coating.

SUMMARY

Previously, the significance of the natural buffer capacity near pH 4 of PVP has not been recognized, but it now appears that the presence of a certain, small buffer capacity near pH 4 in the swelling medium is crucial for the stability and the control of bioburden of e.g. urinary catheters with hydrophilic coating, when they are sterilized and stored wet.

The disclosed findings surprisingly indicate that because of the electron beam sterilization there must be a certain amount of buffer present in the swelling media for ready-to-use urinary catheters (i.e. the catheters are stored wet), such as SpeediCath®. Specifically, it is shown that if pH decreases to below 3.7, the hydrophilic coating on the catheters may be ruined. This is presumably because without the buffer, the pH drops to well below 3.7 as a result of acid formation during wet sterilization and subsequent storage. At this low pH the hydrolysis of acid susceptible polymers, such as polyesters, polyurethanes, and polyethers, may be unacceptably high.

The present invention discloses that when a buffer is added to a swelling medium containing hydrophilic polymers with no natural buffer capacity, the shelf life of electron beam-sterilized hydrophilic coatings, that are in contact with the swelling medium, increases. Furthermore, the new proposed swelling medium is not cytotoxic and complies with current safety regulations.

DETAILED DISCLOSURE

One embodiment of the invention relates to a medical device comprising a hydrophilic coating, said medical device being sterilized while in contact with a liquid comprising:
a) a hydrophilic polymer; and
b) a separate buffer.

A related embodiment relates to a sterilised set comprising a medical device comprising a hydrophilic coating in contact with an aqueous liquid comprising:
a) a hydrophilic polymer;
b) a separate buffer;
wherein said set has been sterilised using irradiation while in contact with said liquid.

The device in this composition can be stored for at least 2 years with retention of the dry-out time and friction—factors important to a medical device.

The medical device may be selected from the group consisting of catheters, endoscopes, laryngoscopes, tubes for feeding, tubes for drainage, guide wires, condoms, urisheaths, barrier coatings, stents and other implants, extra corporeal blood conduits, membranes, blood filters, devices for circulatory assistance, dressings for wound care, and ostomy bags. At present most relevant medical devices or medical device elements are catheters and catheter elements.

In one aspect of the invention the sterilization by irradiation is performed by β- or γ-irradiation (beta- or gamma-irradiation).

The swelling medium for SpeediCath® contains PVP C-15 as hydrophilic polymer (as described in WO0030696).

Because of the polymerization chemistry PVP naturally contains one carboxylic acid group per polymer chain, which gives
1) a start pH of about 4 after sterilization, and
2) a small buffer capacity which is, however, large enough to prevent a further pH decrease in the system during β-sterilization (electron beam sterilization) and storage.

The buffer capacity of PVP C-15 is largest between pH 4 and 6.

When PVP C-15 in the SpeediCath swelling medium was substituted with PEG 2000 (which does not naturally contain any carboxylic acid groups) without simultaneous addition of a buffer, the catheters did not survive sterilization and subsequent storage. Although the mechanism of the damage caused by low pH on the hydrophilic coating is not known at present, the presence of a buffer in the system appears to be mandatory.

The currently used swelling medium for SpeediCath® contains 6% PVP C-15 and 0.9% NaCl (for regulation of osmolality). In the pursuit of a swelling medium with a hydrophilic polymer with other properties than PVP C-15 we have observed that a swelling medium containing only 6% PEG 2000 and 0.9% NaCl failed to protect the catheter during electron beam sterilization and subsequent storage at ambient and higher temperatures in an accelerated storage stability test. Use of the swelling medium containing PEG 2000 resulted in catheters with an unacceptably low dry-out time, below the specified 5 minutes, after sterilization and accelerated storage. However, when the biological buffer sodium citrate (or a mixture of sodium citrate and citric acid) was added to the swelling medium containing PEG 2000, the performance of the stored catheters was as good as or better than the performance of catheters stored with the conventional swelling medium containing PVP C-15. One could argue that the swelling medium might be produced without any buffer but instead at a sufficiently high start-pH so that, even after sterilization and prolonged storage, the pH would not fall below 3.7. Whereas this might be true, a swelling medium with a high starting pH would 1) absorb a random amount of $CO_2$ from the air and acquire a variable buffer capacity from the $H_2CO_3/HCO_3^-/CO_3^{2-}$ system, which is undesirable; and 2) quickly develop growth between the time of mixing of the swelling medium and the time of sterilization. Hence the bioburden of a swelling medium without buffer (with a high initial pH) would be much larger than in the current system, and, consequently, the holding time between the manufacture of the swelling medium and the sterilization might become unacceptably low.

In relation to bioburden, the pH of the swelling medium ideally should be as low as possible, but a pH value of about 4 from the time of production to the time of sterilization works very well. The swelling media containing either PVP C-15 or PEG 2000+citrate/citric acid both fulfill this requirement. Whereas the presence of a buffer in the SpeediCath swelling medium is a good idea for the above-mentioned reasons, the buffer capacity (and hence the buffer concentration) should be kept as low as possible, because high buffer capacity correlates with the level of pain in small wounds, and the same situation probably applies to catheter users with small scratches in their urethra. Hence a suitable compromise has been found between conflicting demands for high coating stability (pH>3.7), low bioburden (pH as low as possible, but a pH value of 4 works well), and low buffer capacity (below 4 mM from pH 4 to pH 7.4) in the currently employed recipe for the swelling medium: 6% PEG 2000, 0.88% NaCl, and 0.038% citric acid, adjusted to pH 3.95 with HCl or NaOH.

Suitable separate buffers for addition to hydrophilic polymers without natural buffer capacity should have at least one suitable acid strength constant, $K_a$, with a $pK_a$ value between 2 and 6, such as between 2.5 and 5.5, and more preferred between 2.7 and 5. $K_a$ and $pK_a$ are defined for the acid-base equilibrium $HA \leftrightharpoons H^+ + A^-$ in water as follows:

$$K_a = [H^+] \times [A^-]/[HA]; pK_a = -\log_{10}(K_a)$$

The minimum $pK_a$ value of 2.7 ensures a reasonable buffer capacity at pH 3.7, which is the minimum allowable pH during sterilization and subsequent storage. Conversely, the maximum $pK_a$ value of 5.0 ensures a reasonable buffer capacity at the preferred starting pH of 4.0. Buffers that fulfill these requirements include monocarboxylic acids, such as formic acid ($pK_a$=3.75), acetic acid (4.75), propionic acid (4.87), 3-hydroxypropionic acid (3.73), 2,3-dihydroxypropionic acid (3.64), gluconic acid (3.56), benzoic acid (4.19), cis-cinnamic acid (3.89), trans-cinnamic acid (4.44), lactic acid (3.85), mandelic acid (3.85), glycolic acid (3.83), phenylacetic acid (4.28), o-chlorobenzoic acid (2.92), m-chlorobenzoic acid (3.82), p-chlorobenzoic acid (3.98), 1-naphthoic acid (3.70), 2-naphthoic acid (4.17), o-toluic acid (3.91), m-toluic acid (4.27), p-toluic acid (4.36), N-acetylglycine (3.67), and hippuric acid (3.80); dicarboxylic acids, such as oxalic acid ($pK_{a1}$=1.23, $pK_{a2}$=4.19), malonic acid ($pK_{a1}$=2.83, $pK_{a2}$=5.69), succinic acid ($pK_{a1}$=4.16, $pK_{a2}$=5.61), glutaric acid ($pK_{a1}$=4.31, $pK_{a2}$=5.41), adipic acid ($pK_{a1}$=4.43, $pK_{a2}$=5.41), pimelic acid ($pK_{a1}$=$pK_{a2}$=4.71), phthalic acid ($pK_{a1}$=2.89, $pK_{a2}$=5.51), isophthalic acid ($pK_{a1}$=3.54, $pK_{a2}$=4.60), terephthalic acid ($pK_{a1}$=3.51, $pK_{a2}$=4.82), 1,1-cyclohexanedicarboxylic acid ($pK_{a1}$=3.45, $pK_{a2}$=6.11), malic acid ($pK_{a1}$=3.40, $pK_{a2}$=5.11), α-tartaric acid ($pK_{a1}$=2.98, $pK_{a2}$=4.34), meso-tartaric acid ($pK_{a1}$=3.22, $pK_{a2}$=4.82), itaconic acid ($pK_{a1}$=3.85, $pK_{a2}$=5.45), and fumaric acid ($pK_{a1}$=3.03, $pK_{a2}$=4.44); tri- and tetracarboxylic acids, such as citric acid ($pK_{a1}$=3.14, $pK_{a2}$=4.77, $pK_{a3}$=6.39) and 1,2,3,4-butanetetracarboxylic acid ($pK_{a1}$=3.36, $pK_{a2}$=4.38, $pK_{a3}$=5.45, $pK_{a4}$=6.63); amino acids, such as tryptophan ($pK_{a1}$=2.83, $pK_{a2}$=9.39), aspartic acid ($pK_{a1}$=1.88, $pK_{a2}$=3.65, $pK_{a3}$=9.60), glutamic acid ($pK_{a1}$=2.19, $pK_{a2}$=4.25, $pK_{a3}$=9.67), anthranilic acid (o-aminobenzoic acid; $pK_{a1}$=2.11, $pK_{a2}$=4.95), m-aminobenzoic acid (4.78), p-aminobenzoic acid ($pK_{a1}$=2.50, $pK_{a2}$=4.87), glutathione (3.59), glycylglycine (3.14), glycylglycylglycine ($pK_{a1}$=3.23, $pK_{a2}$=8.09), N-phenylglycine ($pK_{a1}$=1.83, $pK_{a2}$=4.39), carnosine (β-alanylhistidine; $pK_{a1}$=2.73, $pK_{a2}$=6.87, $pK_{a3}$=9.73), niacin (3-pyridinecarboxylic acid; 4.85), 4-pyridinecarboxylic acid (4.96); aminosulphonic acids, such as m-aminobenzenesulfonic acid (3.73), and sulfanilic acid (p-aminobenzenesulfonic acid; 3.23); and inorganic acids, such as hydrofluoric acid (3.45), cyanic acid (3.92), and nitrous acid (3.37). Most $pK_a$ values are from various editions of The CRC Handbook of Chemistry and Physics, published by The Chemical Rubber Company.

The preferred buffers have:
1. As high buffer capacity as possible between the starting pH of 4.0 and the minimum allowable pH of 3.7 in order to prevent pH from falling in this range during β-sterilization and subsequent storage.
2. As low buffer capacity as possible between pH 4.0 and pH 7.4 in order to minimize the pain felt by users with a damaged urethra.

Hence especially preferred buffers include compounds with only one buffer active group with a $pK_a$ value between 3.7 and 4.0 such as the monocarboxylic acids, formic acid, cis-cinnamic acid, lactic acid, 3-hydroxypropionic acid, mandelic acid, glycolic acid, 1-naphthoic acid, o-toluic acid, m-chlorobenzoic acid, p-chlorobenzoic acid, N-acetylglycine, hippuric acid, m-aminobenzenesulfonic acid, and the inorganic cyanic acid. Especially preferred buffers with several buffer active groups (such as di-, tri- or polyacids, or amino acids) include compounds with one or several $pK_a$ values between 3.7 and 4.0 and the other pKa values smaller than 3.7 or larger than 8.9 (so the buffer capacity between 4.0 and 7.4 is negligible), such as aspartic acid and glutathione.

Buffers with the largest $pK_a$ value below 3.7 are slightly less preferred because of their rather low buffer capacity at pH 4.0. However, if very low buffer capacity between pH 4.0 and 7.4 is of paramount importance, then buffers with the largest $pK_a$ value below 3.7 are ideal; these include 2,3-dihydroxypropionic acid, gluconic acid, o-chlorobenzoic acid, glycylglycine, sulfanilic acid, hydrofluoric acid, and nitrous acid. Slightly less preferred buffers with several buffer active groups include compounds with one or several $pK_a$ values below 3.7 and the other pKa values larger than 8.9, such as tryptophan.

Buffers with one or several $pK_a$ values between 4.0 and 8.9 are less preferred, because their buffer capacities between 4.0 and 8.9 do not contribute very much to the stabilization of pH between 3.7 and 4.0 and, at the same time, may contribute significantly to the pain felt by the user. However, it is still better to employ one of these buffers than none at all; they include acetic acid, propionic acid, benzoic acid, trans-cinnamic acid, phenylacetic acid, 2-naphthoic acid, m-toluic acid, p-toluic acid, oxalic acid, malonic acid, succinic acid, glutaric acid, adipic acid, pimelic acid, phthalic acid, isophthalic acid, terephthalic acid, 1,1-cyclohexanedicarboxylic acid, malic acid, α-tartaric acid, meso-tartaric acid, itaconic acid, fumaric acid, citric acid, 1,2,3,4-butanetetracarboxylic acid, glutamic acid, glycylglycylglycine, anthranilic acid, m-aminobenzoic acid, p-aminobenzoic acid, N-phenylglycine, carnosine, niacin, and 4-pyridinecarboxylic acid.

The buffer capacity, β, of the swelling media was measured as it is standard in the art, see e.g. Niels Linnet: "pH measurements in theory and practice", 1. ed., Radiometer A/S, Copenhagen, 1970:

$$\beta = db/dpH$$

where db is the amount of strong base (measured in moles) per liter of the swelling medium required to bring about the pH change dpH in the solution. If, for example, 0.13 mL 0.1 M NaOH (=0.013 mmol=13 μmol) was required to raise pH from 7.40 to 7.94 in 20 mL of a certain swelling medium, then the buffer capacity, β, at pH 7.67 (the mean value of 7.40 and 7.94) was:

$$\beta(7.67) = db/dpH = (0.65 \text{ μmol/mL NaOH})/(7.94-7.40) = 1.2 \text{ μmol/(pH×mL)} = 1.2 \text{ mM/pH}$$

Hence the more NaOH that was needed to raise the pH by a certain amount, the higher the buffer capacity. According to theory the maximum buffer capacity of a buffer active substance is found at $pH = pK_a$ of the group and is equal to 0.576 times the concentration of the buffer active group.

Buffer capacity data are presented below as the number of micromoles of NaOH required to bring 1 mL swelling medium from pH 4.0 to 7.4. The unit of this buffer capacity is μmol/mL=mmol/L=mM. In some cases the buffer capacity was measured as the number of micromoles of HCl required to bring 1 mL swelling medium from pH 7.4 to 4.0. The titrations with NaOH and HCl should in principle give exactly the same buffer capacity, but in reality the buffer capacity measured from the HCl titration is slightly higher than the buffer capacity from the NaOH titration. This is because the HCl titration moves from high to low pH, that is from an alkaline to an acidic solution, and it is difficult to prevent the alkaline sample from absorbing $CO_2$ from the air. As noted above, $CO_2$ will be converted in the alkaline sample to buffer-active $CO_3^{2-}$ or $HCO_3^-$, and this will give rise to an artificially high reading of buffer capacity. However, control measurements showed that this was no problem in the present system.

In a preferred embodiment of the invention, the buffer capacity of the separate buffer is below 8, such as below 7, preferably below 6, or even 5, most preferably below 4 mM in the interval from pH 4 to pH 7.4.

In one embodiment of the invention, the separate buffer is a different chemical entity than the hydrophilic polymer. That is, e.g. that is it has a different GC or HPLC spectrum from the hydrophilic polymer.

In a preferred embodiment the wetting liquid, that is, the liquid with the hydrophilic polymer and the separate buffer, further comprises an osmolality increasing agent. Osmolality increasing agents include inorganic salts in which the cations or anions have no $pK_a$ values between 2.5 and 8.9, so they do not affect the buffer capacity of the buffer component between pH 4.0 and 7.4. Such inorganic salts include any combination of a cation [e.g. tetraalkylammonium, trialkylammonium, dialkylammonium, monoalkyammonium, ammonium, an alkali metal (i.e. lithium, sodium, potassium, etc.), an alkaline earth metal (i.e. magnesium, calcium, etc.), or a trivalent metal (i.e. scandium, yttrium, lanthanum, etc.)] with an anion [e.g. chloride, bromide, iodide, nitrate, perchlorate, chlorate, bromate, iodate, chlorite, thiocyanate, hydrogen sulfate, methanesulfonate, trifluoromethanesulfonate, benzenesulfonate, p-toluenesulfonate, sulfate, thiosulfate, carbonate, or phosphate]. Other examples of osmolality increasing agents are organic, low molecular weight compounds that are physiologically acceptable and non-irritating, such as, but not limited to, urea or glycerol. The liquid is preferably isotonic in use, that is, the osmolality corresponds to the osmolality of 0.9% NaCl. In principle the desired osmolality could also be achieved by adding a buffer to the solution, such as citrate/hydrogen citrate/dihydrogen citrate/citric acid or benzoate/benzoic acid. The exact concentration of each species in the two buffer systems is governed by the difference between the chosen start pH and the $pK_a$ value(s) of the buffer. However, most buffers have a higher molecular weight than NaCl, and since the osmolality of a dissolved osmolality increasing agent increases linearly with the total molar concentration of neutral molecules and ions (see e.g. P. W. Atkins: "Physical Chemistry", 2. ed., Oxford University Press, London, 1984, pp. 228-33), it follows that in many cases more than 0.9% buffer would be required to obtain the same osmolality as 0.9% NaCl. 0.9% or more of a buffer with one or more $pK_a$ values between 2.5 and 8.9 could incur unacceptable pain to a user with a damaged urethra, so buffers in such amounts should not be used as osmolality increasing agents.

Use the above-mentioned recipe for the swelling medium: 6% PEG 2000, 0.88% NaCl, 0.038% citric acid; adjust pH to 3.95 with HCl or NaOH. As is apparent from the above, citric acid belongs to the class of less preferred buffers. However, the widespread occurrence in biological systems and the non-toxicity of citric acid makes it a good choice for buffer anyway.

One aspect of the present invention utilizes hydrophilic polymers without natural buffer capacity near pH 4, such as near pH 3.7. Thus, their use requires addition of extra buffer.

In various preferred embodiments, the hydrophilic polymer without natural buffer capacity near pH 4 is selected from the group consisting of poly(meth)acrylic acid esters; poly(meth)acrylamides with or without N-alkyl substitution; poly(vinyl alcohol); partially saponified poly(vinyl acetate); poly(ethylene glycol); poly(ethylene glycol-co-propylene glycol); poly(ethylene glycol)-poly(propylene glycol) block copolymers; copolymers and block copolymers of ethylene glycol and other 1,2-epoxide monomers, such as 1-butene oxide, cis- and trans-2-butene oxide, cyclopentene oxide, cyclohexene oxide, and styrene oxide; poly(vinyl methyl ether); poly(2-ethyl-4,5-dihydrooxazole) (e.g. available in various molecular weights as Aquazol from ISP Corporation) and other 2-substituted poly(4,5-dihydrooxazole)s; poly(2-vinyl-1-(3-sulfopropyl)pyridinium inner salt); poly(2-vinyl-1-(4-sulfobutyl)pyridinium inner salt); poly(2-methyl-5-vinyl-1-(3-sulfopropyl)pyridinium inner salt); poly(4-vinyl-1-(3-sulfopropyl)pyridinium inner salt); poly(4-vinyl-1-(4-sulfobutyl)pyridinium inner salt); poly(N,N-dimethyl-N-2-methacryloyloxyethyl-N-(3-sulfopropyl)ammonium inner salt); poly(N,N-dimethyl-N-3-methacrylamidopropyl-N-(3-sulfopropyl)ammonium inner salt); poly(N,N-diethyl-N-methacryloyloxyethoxyethyl-N-(3-sulfopropyl)ammonium inner salt); poly(4-vinyl-N-methylpyridinium-co-p-styrenesulfonate); poly(N,N,N-trimethyl-N-3-methacrylamidopropylammonium-co-2-acrylamido-2-methylpropanesulfonate); poly(methacryloyloxyethyltrimethylammonium-co-2-methacryloyloxyethanesulfonate); poly(N-oxide)s, such as poly(2-vinylpyridine-N-oxide) and poly(4-vinylpyridine-N-oxide); poly(vinylsulfonic acid) and salts; poly(styrenesulfonic acid) and salts; poly(2-methacryloyloxyethanesulfonic acid) and salts; poly(3-methacryloyloxy-2-hydroxypropanesulfonic acid) and salts; poly(2-acrylamido-2-methylpropanesulfonic acid) and salts; poly(3-vinyloxypropanesulfonic acid) and salts; salts of polycarbamoyl sulfonates; salts of sulfonated ethylene-propylene-diene terpolymers; poly(4-vinylbenzyltrimethylammonium salt with a mono- or divalent anion); poly(diallyldimethylammonium salt with a mono- or divalent anion); poly(diallyldiethylammonium salt with a mono- or divalent anion); poly(methacryloyloxyethyltrimethylammonium salt with a mono- or divalent anion); poly(methacryloyloxyethyltriethylammonium salt with a mono- or divalent anion); poly(methacryloyloxypropyltrimethylammonium salt with a mono- or divalent anion); poly(methacryloyloxypropyltriethylammonium salt with a mono- or divalent anion); poly(N-alkyl-2-vinylpyridinium salt with a mono- or divalent anion); poly(N-alkyl-4-vinylpyridine salt with a mono- or divalent anion); and polyurethane ionomers containing tetraalkylammonium groups with mono- or divalent anionic counterions, as described in Encyclopedia of Polymer Science and Engineering, eds. H. F. Mark, N. M. Bikales, C. G. Overberger, and G. Menges, 2. ed., vol. 13, pp. 292-4, Wiley-Interscience, New York, 1988. The cations used for the salts, and the mono- or divalent anions should have no $pK_a$ values between 2.5 and 8.9, so that they do not affect the buffer capacity of the buffer component between pH 4.0 and 7.4. Appropriate cations for the salts include tetraalkylammonium, trialkylammonium, dialkylammonium, monoalkykammonium, ammonium, alkali metals (i.e. lithium, sodium, potassium, etc.), alkaline earth metals (i.e. magnesium, calcium, etc.), and some trivalent metals (i.e. scandium, yttrium, lanthanum, etc.). Appropriate monovalent anions include chloride, bromide, iodide, nitrate, perchlorate, chlorate, bromate, iodate, chlorite, thiocyanate, hydrogen sulfate, methanesulfonate, trifluoromethanesulfonate, benzenesulfonate, and p-toluenesulfonate. Appropriate divalent anions include sulfate, thiosulfate, and carbonate. In other preferred embodiments, the hydrophilic polymer is a copolymer of any of the monomers without natural buffer capacity near pH 4. Further preferred hydrophilic polymers without natural buffer capacity near pH 4 include the group of polysaccharides without carboxylic acid groups (possibly partially hydrolyzed in order to improve solubility and avoid gelation during β-sterilization), such as agarose; ι-, κ-, λ-, μ-, and ν-carrageenan, and furcellaran; guaran gum; locust bean gum; tamarind flour; scleroglucan; schizophyllan; pseudonigeran; nigeran; isolichenan; amylose; amylopectin; starch and alkylated derivatives, such as hydroxyethylstarch; glycogen; pullulan; dextran; callose; curdlan; pachyman; laminaran; lichenan; cellulose and alkylated derivatives, such as hydroxyethylcellulose or hydroxyproylcellulose; pustulan; alkylated derivatives of chitin, such as hydroxyethylchitin; inulin; levan; α-L-arabinofuranans (e.g. xylopyranoarabinofuranans); β-D-galactans (e.g. arabinogalactans, for example from Larix species); α-D-mannans (e.g. xylomannans; arabinoxylomannans; rhamnomannans; glucomannans; galactofuranomannans); β-D-mannans (e.g. galactomannans); and β-D-xylans (e.g. rhodymenan and arabinoxylans).

A large number of methods are known for the production of hydrophilic surface coatings for improving the slipperiness of a catheter or other medical device. These methods are most often based on the fact that the substrate to be provided with a hydrophilic surface coating, in the course of one or more process stages with intermediary drying and curing, is coated with one or more (most often two) layers, which are brought to react with one another in various ways, e.g. by polymerisation initiated by irradiation, by UV light, by graft polymerisation, by the formation of inter-polymeric network structures, or by direct chemical reaction. Known hydrophilic coatings and processes for the application thereof are e.g. disclosed in Danish Patent No. 159,018, published European Patent Application Nos. EP 0 389 632, EP 0 379 156, and EP 0 454 293, European Patent No. EP 0 093 093 B2, British Patent No. 1,600,963, U.S. Pat. Nos. 4,119,094, 4,373,009, 4,792,914, 5,041,100 and 5,120,816, and into PCT Publication Nos. WO 90/05162 and WO 91/19756.

In a preferred embodiment the hydrophilic coating is a PVP coating. Such coating contains PVP bound to the medical device.

EXAMPLES

The present examples illustrate various aspects of the invention. We conclude that if sterilization is performed with a buffer with a $pK_a$ value between 2.7 and 5, the coating is protected against acid degradation. Although a low buffer capacity between pH 4.0 and 7.4 reduces pain for the user, we have also performed experiments with high buffer concentrations in order to test their influence on the various quality parameters of the hydrophilic coating. We prefer that pH is about 4.0 at the time of production in order to minimize the formation of bacteria in the swelling media prior to sterilization (that is, to reduce the bioburden).

The purpose of the experiments was to investigate whether it was possible to substitute PVP with PEG 2000 for the swelling medium for hydrophilic coated catheters (e.g. the SpeediCath® catheter).

The present examples confirm the findings previously published in WO06117372, where the immediate effect of PEG 2000 was illustrated in example 8, table 3. In that experiment the friction force and the water retention were measured shortly after β-sterilization. However, the present data illustrate degradation of the coating when stored under standard storage-test conditions and suggest that this degradation can be avoided by control of pH through addition of a buffer.

Example 1

Testing of PEG 2000 with and without Citrate Buffer

We evaluated the storage stability of different coatings with the standard (PVP C-15) and the new (PEG 2000) as hydrophilic polymer in the swelling medium. Extra buffer was added to some of the swelling media, and a control without hydrophilic polymer in the swelling medium was also evaluated. The experiment was conducted according to ICH guidelines (International Conference on Harmonisation of Technical Requirements for Registration of Pharmaceuticals for Human Use). The applied guidelines were "Stability Testing of New Drug Substances and Products, Q1A(R2)" and "Evaluation for Stability Data, Q1E).

Swelling Media
Liquid A: 5.0 kg 6% PEG 2000, 0.9% NaCl
Liquid B: 2 kg 6% PVP C-15, 0.9% NaCl
Liquid C: 2 kg 0.9% NaCl
Liquid D: 2.5 kg 6% PEG 2000, 3% trisodium citrate dihydrate
Liquid E: 2.5 kg 6% PEG 2000, 2.0000% trisodium citrate dihydrate, and 0.6532% anhydrous citric acid or 0.7145% citric acid monohydrate.

Catheters
Cath 1: 800 male SpeediCath® CH12 catheters with hydrophilic coating from the same production batch (batch 1). These were used for all five liquids A-E.
Cath A2: 110 male SpeediCath® CH12 catheters with hydrophilic coating from another production batch (batch 2). These were used exclusively with liquid A.
Cath A3: 110 male SpeediCath® CH12 catheters with hydrophilic coating from a third production batch (batch 3). These were used exclusively with liquid A.

For Cath 1, 2 and 3 the following rule applied: The batch was included if the friction of each of 3 coated, unsterilized catheters, which had swelled in de-ionized water for at least 30 seconds, was below 100 mN. The results from Cath 1, Cath 2 and Cath 3 were pooled in the Results section below, unless otherwise noted.

A hydrophilic, crosslinked dip coating based on PVP K-90 was used for the SpeediCath® catheters.
PEG 2000 was from Clariant.
PVP C-15 and PVP K-90 were from ISP.
Polyurethane catheters were obtained from Unomedical A/S.
Hydrophilic polyurethanes were available from several sources, e.g. CardioTech and Thermedics (Lubrizol).

Packaging of Catheters
The following number of catheters (Cath 1, Cath 2, Cath 3) from different batches was packaged with 12 mL of one of the swelling media (A, B, C, D, E).

| Catheter batch | Liquid | | | | |
|---|---|---|---|---|---|
| | A | B | C | D | E |
| Cath 1 | 160 (A1) | 160 (B1) | 160 (C1) | 160 (D1) | 160 (E1) |
| Cath 2 | 110 (A2) | — | — | — | — |
| Cath 3 | 110 (A3) | — | — | — | — |

Storage of Catheters
The 160 samples labeled A1 were distributed on the 16 different storage conditions below with 10 identical samples at each storage condition. The foils were further labeled with the text in the scheme. For most measurements, data from 0 to 12 months storage were available; however, in some cases only data from 0 to 9 months storage were available. The 160 samples labeled B1, C1, D1 and E1 were distributed and labeled similarly:

| Storage temp. (deg. C.) | Storage time (months) | | | | | | | |
|---|---|---|---|---|---|---|---|---|
| | 0, before sterilization | 0, after sterilization | 3 | 6 | 9 | 12 | 18 | 24 |
| 23 | 23-FS | 23-ES | 23-3 | 23-6 | 23-9 | 23-12 | 23-18 | 23-24 |
| 40 | | | | 40-6 | | 40-12 | | 40-24 |
| 50 | | | 50-3 | 50-6 | | 50-12 | | |
| 60 | | | 60-3 | 60-6 | | | | |

The 110 samples labeled A2 and the 110 samples labeled A3 were distributed at the 11 storage conditions below with 10 identical samples at each condition. They were further labeled according to the text in the scheme:

| Storage temp. (deg. C.) | Storage time (months) | | | | | | | |
|---|---|---|---|---|---|---|---|---|
| | 0, before sterilization | 0, efter sterilization | 3 | 6 | 9 | 12 | 18 | 24 |
| 23 | 23-FS | 23-ES | 23-3 | 23-6 | 23-9 | 23-12 | 23-18 | 23-24 |
| 40 | | | | 40-6 | | 40-12 | | 40-24 |

Hence these samples were only stored at 23 and 40 deg. C.
Other SpeediCath male CH12 catheters were packaged with swelling medium F:
  6% PEG 2000, 0.88% NaCl, 0.038% citric acid, pH adjusted to 3.95 with NaOH. The samples are labeled F7 below.

Sterilization

The A1 to E1 samples all contained packaged catheters in the swelling medium and were sent to 2×25 kGy β-sterilization at Sterigenics in Mørdrup (Denmark) except for the FS-samples (no sterilization), which were evaluated before sterilization. The F7 samples were sterilized at 2×37.5 kGy.

Evaluation of Catheters

In all cases 10 catheters were available at each combination of storage time and storage temperature. These 10 catheters were distributed in the following way:

One catheter was used for determination of cytotoxicity. A piece of the coated catheter was cut off and used for the analysis.

Four catheters were used for the subjective evaluation of dry-out time. The catheters were hanged vertically by the connector either for 3, 5, 7 and 9 minutes (mainly during the start of the storage period and at low storage temperatures, when the catheters had not been extensively damaged), or for 1, 3, 5 and 7 minutes (for catheters that might have been damaged by long storage time or high storage temperature). During the evaluation the index finger and thumb were first moved from the upper part of the catheter and down, then up and down a few times. The operator decided on a score from 0 to 5, where 0 was bone dry and 5 was completely slippery. The dry-out time was defined as the last moment when the score was 3 or higher. As an example, if the score was 5, 5, 4, 3 after 3, 5, 7, and 9 minutes, then the dry-out time was 9 minutes. On the other hand, if the score was 5, 3, 2, 3 after 1, 3, 5, and 7 minutes, then the dry-out time was 3 minutes. This was a single measurement, although four catheters were used. The dry-out time should be at least 5 minutes.

Three catheters were used for subjective evaluation of stability and slipperiness during prolonged rubbing of the catheters between the fingers under running, lukewarm water. Stability and slipperiness were scored on a scale from 0 to 5, where 0 was worst and 5 was perfect. Different catheters, which were evaluated after the same storage time, were evaluated in random order. This was a triple measurement. Ideally, the slipperiness should be at least 4 ("almost perfectly slippery"), and the stability should be 5 ("perfectly stable").

Two catheters were used for friction measurement. A Texture Analyzer was used for measurements on samples A1-E1. The measurements on the Texture Analyser were all done with a load of 266 g and at a speed of 10 mm/s. The length of the friction block was 35 mm and the frictions were measured over 15 cm of the catheters. All tests were started immediately after placing the sample on the analyser and applying the load.

A Friction tester was used for the F7 samples. The measurements on the Friction tester were all done with a load of 164 g at a speed of 4 mm/s. The length of the friction block was 21 mm and the friction was measured over 18.5 cm of the catheter. All tests were started immediately after placing the sample on the Friction tester and applying the load.

The results from these two different measurements were not comparable but are shown anyway to illustrate the development of the friction force at different storage times. In both cases the following procedure was followed:

One catheter was measured immediately after withdrawal from the swelling medium (i.e. after 0 minutes dry-out time);

The other catheter was hanged vertically for 5 minutes in the connector to dry before measurement. This was done in a climate room (i.e. at 23° C. and 60-70% humidity).

The result was evaluated as the mean friction force at the passage of the friction block once over and once back over the catheter. The mass of the friction block and the relative humidity in the laboratory were recorded. These were single measurements. The friction force should be below 150 mN, ideally below 100 mN.

Swelling Media

The swelling medium from the cytotoxicity measurement was used for determination of osmolality, using a cryoscopic osmometer (Osmomat 030-D from Gonotec). Two to three determinations were made on the single sample.

The five pooled swelling media from subjective evaluation and friction were used for determination of buffer capacity and pH.

Results—pH, Buffer Capacity and Osmolality of the Swelling Media

The pH measurements are shown in FIG. 1 to FIG. 4 for storage at 23, 40, 50 and 60° C. pH of the samples {NaCl} (without any hydrophilic polymer or buffer) and {PEG+NaCl} (without buffer) decreased quickly and steadily during storage to a very low level, probably because of the formation of carboxylic acids. The formation of carboxylic acids in sample {NaCl} could be due to oxidation of the polyethylene liner of the packaging material. Apparently the lack of buffer in {NaCl} and {PEG+NaCl} made these samples susceptible to the pH drop that accompanied the formation of carboxylic acids. By contrast, at all temperatures and times the pH of the samples {PEG+citric acid} and {PVP+NaCl} remained roughly constant, whereas the pH of {PEG+citrate} decreased somewhat after sterilization and then remained constant. The pH of the sample {PEG+0.04% citric acid} increased upon sterilization but then decreased a bit after 2 weeks at 60° C. Hence the pH of the {PEG+0.04% citric acid} sample might fall below 3.7 upon further storage; if this should happen, it might be necessary to either produce the swelling medium at a slightly higher starting pH than 3.95 or to increase the concentration of citric acid. The buffer capacity measurements are shown in Table 1.

increase in osmolality of the {PEG+citrate} and {PEG+citric acid} samples from 3 to 6 months at 50° C. was worrying. After storage at 60° C. a more normal pattern was observed: The osmolality of all tested samples increased from 3 to 6 months storage time in the order: {PEG+citric acid}<{NaCl}≈{PVP+NaCl}<{PEG+citrate}<{PEG+

TABLE 1

Buffer capacities of selected samples.

| Sample | Description | Buffer capacity between pH 4.0 and 7.4 (mM) |
|---|---|---|
| A1 23 ES | {PEG + NaCl} after sterilization | 1.14 |
| A1 23-12 | Sterilized {PEG + NaCl} after 12 months at 23 deg. C. | 1.65 |
| A1 40-12 | Sterilized {PEG + NaCl} after 12 months at 40 deg. C. | 6.62 |
| A1 50-12 | Sterilized {PEG + NaCl} after 12 months at 50 deg. C. | 23.8 |
| B1 23 FS | {PVP + NaCl} before sterilization | 7.62 |
| B1 23 ES | {PVP + NaCl} after sterilization | 4.47 |
| B1 50-12 | Sterilized {PVP + NaCl} after 12 months at 50 deg. C. | 8.97 |
| D1 23 FS | {PEG + citrate} before sterilization | 194 |
| D1 23 ES | {PEG + citrate} after sterilization | 187 |
| D1 50-12 | Sterilized {PEG + citrate} after 12 months at 50 deg. C. | 205 |
| E1 23 FS | {PEG + citric acid} before sterilization | 197 |
| E1 23 ES | {PEG + citric acid} after sterilization | 184 |
| E1 50-12 | Sterilized {PEG + citric acid} after 12 months at 50 deg. C. | 165 |
| F7 23 FS | {PEG + NaCl + 0.04% citric acid} before sterilization | 4.01 |
| F7 23 ES | {PEG + NaCl + 0.04% citric acid} after sterilization | 4.80 |
| F7 23-½ | Sterilized {PEG + NaCl + 0.04% citric acid} after 2 weeks at 23 deg. C. | 4.37 |
| F7 60-½ | Sterilized {PEG + NaCl + 0.04% citric acid} after 2 weeks at 60 deg. C. | 4.78 |

The buffer capacity of the A1 samples with unbuffered PEG 2000 increased dramatically with increasing temperature after 12 months storage as a sign that extensive oxidation and degradation of the PEG 2000 took place and produced a large amount of buffer active carboxylic acids. On the other hand, the B1, D1, E1 and F7 samples, which all contained buffer, only showed a small increase in the buffer capacity or even a decrease. Hence the production of carboxylic acids was effectively halted by the presence of a buffer, even the low concentration of buffer in the F7 sample. This indicated that the production of carboxylic acids only proceeded at a low pH, possibly in a sort of autocatalytic process.

The osmolality data are shown in FIG. 5 to FIG. 8. The osmolality is a measure of the number of ions and neutral species that are dissolved in the swelling medium. The information obtained from this measurement is hence related to measurements of pH and buffer capacity. However, whereas the formation of a rather small number of new carboxylic acid groups may decrease the pH and increase the buffer capacity greatly, the osmolality is a bulk property, so only major changes in the number of dissolved species will be recorded.

At 23 and 40° C. most osmolalities decreased slightly, except for the osmolality of {PEG+NaCl}, which increased sharply from 6 to 12 months storage at 40° C. This indicated degradation of the PEG 2000 to smaller fragments. No such degradation was seen in the buffered PEG samples or in the PVP sample. At 50° C. the {PEG+NaCl} sample exhibited the same behaviour, i.e. a sharp rise in osmolality from 6 to 12 months. By contrast, the osmolality of the {PEG+citrate} and {PEG+citric acid} samples went through a maximum after 6 months and then decreased after 12 months at 50° C. We have no good explanation for this, but it is possible that during the first part of the PEG degradation in these samples a lot of small, polymerizable substances were produced (e.g. hydroxy acids or diols+diacids), which then polymerized to polyesters at longer storage times with a simultaneous lowering of the osmolality as result. In any case the rather large NaCl}. Hence the number of dissolved species in the unbuffered PEG samples increased a lot more than that of the other samples, indicating a greater rate of degradation of PEG 2000 without buffer than with buffer. Furthermore, after 2 weeks at 60° C. the osmolality of the {PEG+0.04% citric acid} sample remained constant, as an indication that no extensive degradation of the PEG 2000 had taken place.

Results—Dry-Out Time, Friction, Subjective Slipperiness, and Subjective Stability of the Hydrophilic Coating The dry-out time of the samples is illustrated in FIG. 9 to FIG. 12. Sample {NaCl} without any hydrophilic polymer in the swelling medium had a lower dry-out time than the other samples after 6 months at any storage temperature and, in most cases, also after 3 months. This implied that the presence of a hydrophilic polymer in the swelling medium was important to maintain a high dry-out time of the catheters during prolonged storage. At 50 and 60° C. the dry-out time of the unbuffered {PEG+NaCl} sample was higher than that of the {NaCl} sample but lower than that of {PEG+citric acid}, {PEG+citrate}, and {PVP+NaCl}, all of which had some buffer capacity near pH 4. Hence it seemed that the buffer capacity near pH 4 of those solutions protected the water-binding ability of the hydrophilic coating during storage at high temperatures. However, at 40° C. the {PEG+NaCl} sample actually had the highest dry-out time of any sample at all storage times, and at 23° C. the {PEG+NaCl} sample was in the middle of the field. At present we cannot explain these observations satisfactorily. Suffice it to say that at the most strenuous storage conditions, i.e. the highest temperatures, both a hydrophilic polymer and a buffer must be present in order to retain the initially high dry-out time during storage. Unfortunately no data were available for the sample {PEG+0.04% citric acid}.

The dynamic friction force was evaluated on two separate catheters after 0 and 5 minutes dry-out time in a climate controlled room. The friction after 5 minutes dry-out time was especially important, as it represented a worst-case scenario in relation to the situation of the catheter user. Only data up to 9 months storage were available at the time of writing. As noted above, the friction of the {PEG+0.04% citric acid} samples and the other samples were measured using two different setups. However, the results are shown in the same graphs in order to illustrate the trends in friction with increasing storage time. All frictions after 0 minutes dry-out time are shown in FIG. 13 to FIG. 16. The frictions after 5 minutes dry-out time are shown in FIG. 17 to FIG. 20 except for all data from the {NaCl} sample (C1), which are compiled in Table 2, and data from the {PEG+NaCl} sample (A1) at 60° C., which are shown in Table 3. Hence Table 2 is a supplement to FIG. 17 to FIG. 20, and Table 3 is a further supplement to FIG. 20 only.

TABLE 2

Friction (mN) of {NaCl} sample (C1) after 5 minutes dry-out time

| Temp. (deg. C.) | Before st. | After st. | 3 months | 6 months | 9 months |
|---|---|---|---|---|---|
| 23 | 77 | 818 | 720 | 532 | 1389 |
| 40 | | | — | 1107 | — |
| 50 | | | 902 | 372 | — |
| 60 | | | 779 | 374 | — |

TABLE 3

Friction (mN) of {PEG + NaCl} sample (A1) after 5 minutes dry-out time

| Temp. (deg. C.) | Before st. | After st. | 3 months | 6 months |
|---|---|---|---|---|
| 60 | 130 | 87 | 838 | 297 |

Focussing first on the {NaCl} sample without any hydrophilic polymer in the swelling medium, the friction after 0 minutes dry-out time of the hydrophilic coating increased when it was sterilized. This was in contrast to all the other samples, whose friction decreased upon sterilization. Furthermore, the friction of the {NaCl} sample increased to a higher level than that of the other samples when it was stored at any temperature. This implied that the hydrophilic coating of the catheter was degraded during sterilization and subsequent storage when no hydrophilic polymer was present in the swelling medium. More dramatically, the data for the {NaCl} sample after 5 minutes dry-out time showed that the hydrophilic coating reached a barely measurable friction force of 818 mN (see Table 2) and hence was outright destroyed by sterilization. The mechanism of this destruction was not known, but it obviously involved the absence of hydrophilic polymer. The friction of all other samples, all of which contained hydrophilic polymer in the swelling medium, decreased during sterilization. This signified that in the presence of hydrophilic polymer in the swelling medium, the hydrated, hydrophilic coating crosslinked further and hence became more slippery during sterilization.

However, there were also individual differences between the swelling media that contained hydrophilic polymer. After 0 minute dry-out time at the longest storage times there was a tendency that especially the friction of the {PEG+NaCl} sample, but also that of the {PVP+NaCl}, sample was a bit higher than the friction of the other samples. The friction of the {PEG+0.04% citric acid} was very low before and after sterilization and after 2 weeks storage at either 23 or 60° C. However, as noted above, the trend of the measurements is the most interesting observation here, as these results and the other results are not strictly comparable. After 5 minutes of dry-out time, the friction of the unbuffered {PEG+NaCl} sample was higher than the friction of the other samples at the longest storage times at 40° C. (FIG. 18), 50° C. (FIG. 19) and, especially, at 60° C. (Table 3). The {PEG+citrate} sample had a relatively high friction at 23 and 50° C., and the {PVP+NaCl} sample reached an elevated friction force after 6 months storage at 50° C. (FIG. 19). The friction of the {PEG+0.04% citric acid} sample increased slightly after 2 weeks at 23° C. and a bit more after 2 weeks at 60° C., but the results were still very satisfactory. These measurements led to two general conclusions: (1) The swelling medium must contain a hydrophilic polymer in order to protect the hydrophilic coating during β-sterilization and subsequent storage, and (2) the protective action of the hydrophilic polymer was greatly enhanced by the presence of some buffer capacity (either naturally, as in PVP, or "artificially" from an added buffer) in the system.

The subjective measurement of the slipperiness of the hydrophilic coatings might seem superfluous compared to the objective measurement of friction that was presented above. In reality, however, the human fingertips are a very sensitive measuring instrument, which may sense certain features about the coating that would never be revealed by the friction measurement, such as possible inhomogeneity of the samples (e.g. from dry spots), and lack of smoothness (e.g. from a grainy coating). Therefore the subjective slipperiness was an important supplement to the objective friction measurement. The results are presented in FIG. 21 to FIG. 24; no results were available for the {PEG+0.04% citric acid} sample. The {NaCl} sample without hydrophilic polymer received the lowest rating at all storage times and storage temperatures indicating that the hydrophilic coating of these samples was less pleasant to touch than the other samples. The unbuffered sample {PEG+NaCl} had also been damaged after 3 and 6 months at 60° C., whereas the buffered samples displayed an acceptable subjective slipperiness at all storage conditions. This indicated (1) the crucial need to have a hydrophilic polymer in the swelling medium, and (2) the less than crucial but still important need to have a buffer in the swelling medium.

The subjective stability of the hydrophilic coatings is shown in FIG. 25 to FIG. 28. The majority of the coatings were perfectly stable throughout the storage period at any storage temperature. However, after 12 months storage at 40° C. the hydrophilic coating of the {NaCl} and {PVP+NaCl} samples had loosened somewhat from the substrate catheter, but these samples were not affected at 50 and 60° C. By contrast, after 12 months at 50° C. and after 6 months at 60° C. the {PEG+NaCl} sample was less than perfectly stable, whereas the sample was stable after 12 months at 40° C. Whereas these findings were difficult to rationalize, the fact remained that the coating stability of the {PEG+citric acid} and {PEG+citrate} samples, which both had a large buffer concentration in the swelling medium, was not affected by the storage conditions. Hence the effect of adding a buffer seemed to be beneficial.

Figure 29:
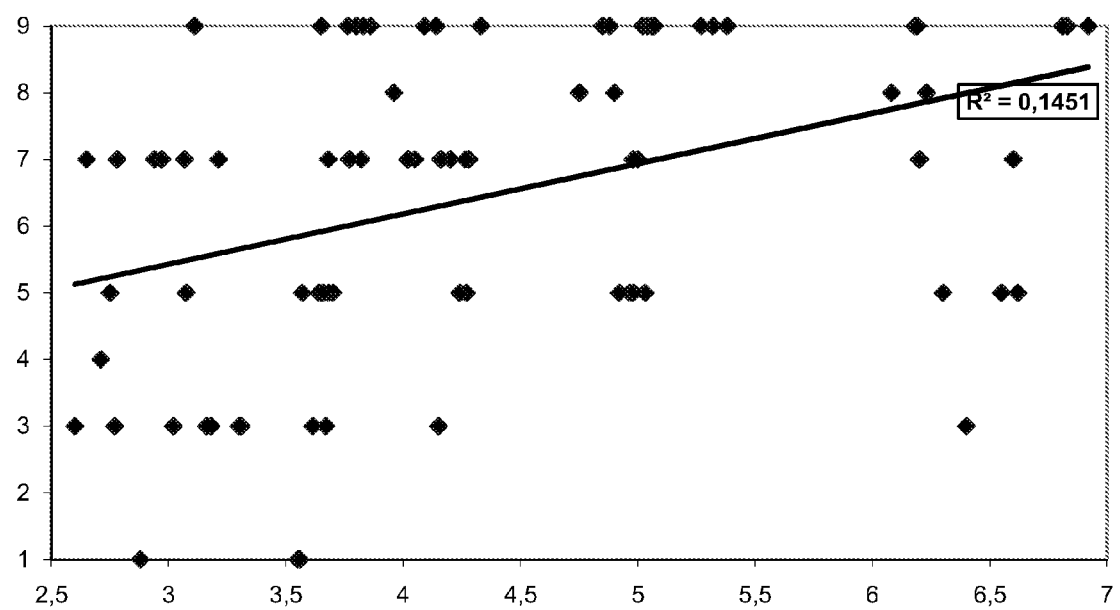
Figure 30:
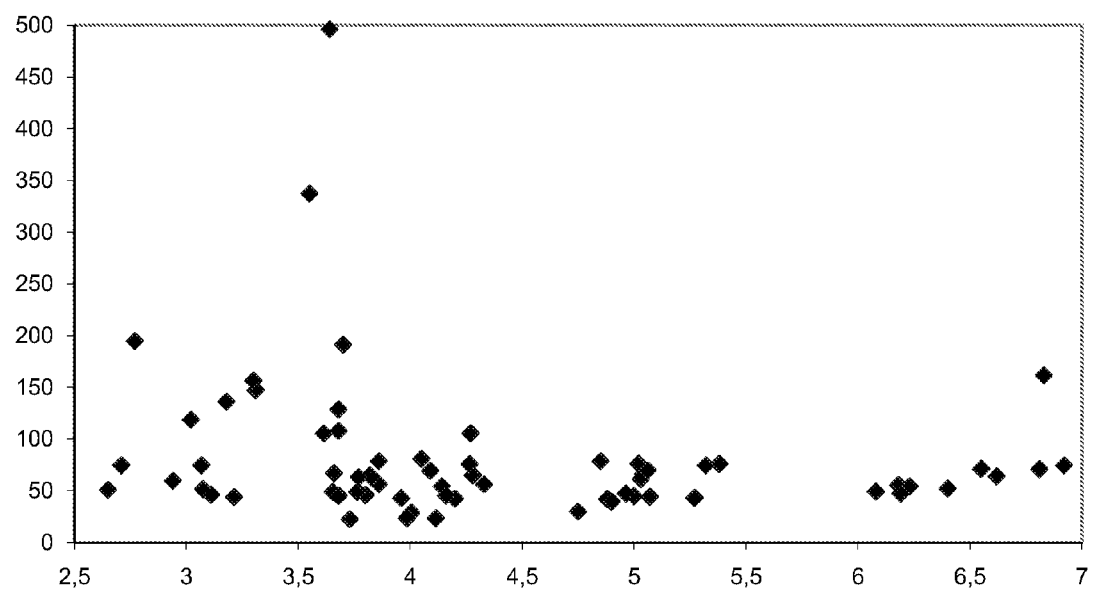

Results—Connection Between pH and the Dry-Out Time, Friction, Subjective Slipperiness, and Subjective Stability of the Hydrophilic Coating In order to get a clearer picture of the relation between pH and the properties of the hydrophilic coating, scatter diagrams were constructed with all the available data across storage temperatures and storage times. These scatter plots are shown in FIG. 29 to FIG. 33. FIG. 29 shows that the dry-out time increased with increasing pH, that is, the lowest dry-out times were found at low pH values. Specifically, at dry-out times of 4 minutes or less, only 2 out of 15 observations were at pH larger than 3.7. Hence low pH seemed to affect the dry-out time negatively. FIG. 30 shows the friction force after 0 minutes dry-out time, that is, the friction of the wet catheters. At pH larger than 4 the frictions were relatively constant, but below pH 4 there seemed to be a slight increase of the mean friction force. More dramatically, however, some very high friction forces (above 190 mN) were observed at and just below pH 3.7 but not at higher pH. This clearly showed that the hydrophilic coating of samples stored at or below pH 3.7 might be severely damaged, so pH should not be allowed to decrease below 3.7. The same pattern, but even more pronounced, was seen in FIG. 31 for the friction force measured on other catheters, that had been allowed to dry in air for 5 minutes before measurement: All frictions above 190 mN were observed at pH less than 3.77, and all frictions above 220 mN at pH less than 3.7. Hence the pH of the products should not be allowed to fall below 3.7, and preferably not even below 3.8. In line with this, in FIG. 32 all values below 4 (on a scale from 0-5) of subjective coating slipperiness occurred at pH below 3.83, and all values below 3.5 were observed at pH 3.7 or lower. Hence these low pH values should be avoided. Lastly, the values of subjective coating stability versus pH are shown in FIG. 33. Although the hydrophilic coating may be damaged in many ways, it is usually stable on the catheter substrate, so in FIG. 33 there were only 5 samples scoring less than 5 on the stability scale from 0 to 5. One of these 5 samples was observed at pH 4.15, whereas the four other samples had pH values below 3.2. Hence, even though there was no clear onset of coating destruction below pH 3.7 in this example, possibly because of the small number of samples with a stability score below 5, the data suggested that the stability of the hydrophilic coating was impaired mainly at low pH values. Together, however, the data presented in FIG. 29 to FIG. 33 presented overwhelming evidence that the pH of the swelling medium should be kept above 3.7, possibly even above 3.8, in order to prevent degradation of the hydrophilic coating on the catheters.

Example 2

Testing of PEG 2000 with Other Buffers

The following swelling media were stored with a male SpeediCath® catheter and electron beam sterilized with a dose of 2×37.5 kGy. Then the osmolality, pH, and buffer capacity to pH 7.4 of the swelling media were measured. Furthermore, the friction of the catheter was measured:

| | | | | After sterilization | | | |
|---|---|---|---|---|---|---|---|
| Sample no. | 6% hydrophilic polymer | 5 mM buffer | Osmolality regulator | Osmolality (mOsmol/kg) | pH | Buffer capacity to pH 7.4 (µM HO⁻) | Friction (mN) |
| 2 | PEG 2000 | Mandelic acid | 155 mM NaCl | 398 | 4.66 | 1.59 | 26 |
| 3 | PEG 2000 | Formic acid | 155 mM NaCl | 400 | 4.18 | 1.52 | 16 |
| 4 | PEG 2000 | Lactic acid | 155 mM NaCl | 398 | 4.20 | 2.42 | 26 |
| 5 | PEG 2000 | Glycolic acid | 155 mM NaCl | 401 | 4.22 | 3.03 | 24 |
| 6 | PEG 2000 | m-Chlorobenzoic acid | 155 mM NaCl | 402 | 3.96 | 1.52 | 19 |
| 8 | PVP C-15 | — | 160 mM NaCl | 405 | 4.25 | 4.60 | 20 |
| 9 | PEG 2000 | Hippuric acid | 155 mM NaCl | 294 | 4.93 | 0.54 | 14 |

Discussion

The osmolality of sample 9 was very low after sterilization. We cannot explain this at present.

The hippuric acid and mandelic acid samples (2 and 9) gave higher pH after sterilization than the rest of the samples. Hence these buffers in particular prevented the pH of the system from falling towards the critical value of 3.7-3.8.

Hippuric acid gave lower buffer capacity after sterilization than any other sample. This should lead to less pain and stinging for the user. The buffer capacities of formic acid, m-chlorobenzoic acid, and mandelic acid were larger than that of hippuric acid but smaller than those of lactic acid and glycolic acid. However, the PVP sample (no. 8) had the highest buffer capacity of any sample, although the pH after sterilization was not particularly low. Hence 5 mM of any of the buffers+155 mM NaCl+6% PEG 2000 gave a swelling medium with lower buffer capacity than that of 160 mM NaCl+6% PVP C-15. At the same time none of the PEG 2000 samples had a pH as low as 3.7-3.8 (which would attack the hydrophilic coating) after sterilization, potentially indicating a long shelf life. Together, these features of the PEG 2000-containing swelling media should prove to be a benefit for users.

Example 3

Bioburden (Antimicrobial Effect) of Swelling Media Containing Peg 2000 and PVP C-15

4 different laboratory cultures were added to aliquots of the different sterile-filtered alternative solutions, which were all at pH 3.95. Samples of 20 ml were then analysed for bioburden by membrane filtration method at day 0, day 1, day 3, day 7 and day 14. The inoculated samples were stored at room temperature. Comparative testing using sterile Peptone water and PVP water was also carried out.

| Solution name | Cultures | Counts in cfu/20 ml | | | | |
|---|---|---|---|---|---|---|
| | | day 0 | day 1 | day 3 | day 7 | day 14 |
| Hippuric acid (5 mM) + 155 mM NaCl + 6% PEG 2000 | B. subtilis | 32 | 3 | 3 | 1 | 0 |
| | E. coli | 75 | 0 | 0 | 0 | 0 |
| | Ps. aeruginosa | 29 | 0 | 0 | 0 | 0 |
| | Asp. niger | 40 | 39 | 22 | 24 | 34 |
| Lactic acid (5 mM) + 155 mM NaCl + 6% PEG 2000 | B. subtilis | 29 | 2 | 4 | 1 | 0 |
| | E. coli | 42 | 1 | 0 | 0 | 0 |
| | Ps. aeruginosa | 29 | 7 | 0 | 0 | 0 |
| | Asp. niger | 37 | 17 | 28 | 20 | 16 |
| Formic acid (5 mM) + 155 mM NaCl + 6% PEG 2000 | B. subtilis | 24 | 4 | 2 | 2 | 0 |
| | E. coli | 55 | 0 | 0 | 0 | 0 |
| | Ps. aeruginosa | 32 | 0 | 0 | 0 | 0 |
| | Asp. niger | 42 | 32 | 40 | 30 | 31 |
| 160 mM NaCl + 6% PVP C-15 | B. subtilis | 16 | 3 | 3 | 2 | 0 |
| | E. coli | 69 | 0 | 0 | 0 | 0 |
| | Ps. aeruginosa | 33 | 0 | 0 | 0 | 0 |
| | Asp. niger | 44 | 21 | 26 | 28 | 23 |
| Peptone water | B. subtilis | 29 | 6 | 1 | 0 | 0 |
| | E. coli | 82 | TNTC | TNTC | TNTC | TNTC |
| | Ps. aeruginosa | 26 | TNTC | TNTC | TNTC | TNTC |
| | Asp. niger | 44 | 51 | 24 | 30 | 33 |

TNTC = too numerous to count

Discussion

B. subtilis, E. coli and Ps. aeruginosa did not survive for long in any of the swelling media. However, B. subtilis also quickly vanished in the reference with Peptone water.

None of the swelling media killed Asp. niger.

It must be stressed that this experiment only pertained to the ability of the microorganisms to survive in the swelling medium after mixing but before electron beam sterilization, after which the counts would all be 0. However, it showed that PEG 2000-containing swelling media were about as antimicrobial after possible contamination during production as swelling media containing PVP C-15.

Example 4

In Vitro Cytotoxicity of Peg 2000 Based Swelling Media

Materials and Methods
Materials
SpeediCath lot. no. 28412 KMI PVP C-15
SpeediCath lot. no. 28412 KMI PEG 2000
Preparation of Samples.

Extracts of the catheters were prepared by cutting the catheters into pieces of 5 cm, containing only the tubing. Three pieces were incubated in a total volume of 9 ml culture medium (DMEM with 10% FCS and Pen/Strep), corresponding to an extraction ratio of 3 ml/cm². The extraction was performed at 37° C. in a humidified atmosphere for 24 hours. The procedures were carried out under aseptic conditions.

At the end of the extraction period, the extraction media were collected and the pH was measured to be 8.0 for all samples. All extraction media were clear without signs of infection. The extracts were not sterile-filtered.

In Vitro Cytotoxicity—Elution Assay

In vitro cytotoxicity analysis was done according to USP25/ISO 10993-5 standard (Elution test). Briefly, murine L929 fibroblasts in a logarithmic growth phase were seeded in 24 well cluster trays at a cell density of $1.5 \times 10^5$ cells/well. The cells were added 2 ml/well growth medium and incubated for 48 hrs at 37° C. in a 95% humidified incubator (5% $CO_2$). Just prior to application of test extracts, the cells were checked to ensure that the cells had a normal morphology and were near-confluent. The culture medium was removed and replaced with undiluted samples and samples diluted 1+3 in culture medium. Culture medium was used as control. All cultures were done in duplicates. Cells were incubated for 48 hrs at 37° C. in an incubator. After the culture period, the cells were analyzed by microscopic evaluation and morphologic changes were recorded as well as the approximate percentage of live cells for each culture. Prior to microscopic assessment, the cultures were incubated with a 0.1% Neutral Red solution to visualize living cells.

TABLE 4

Scoring of cells according to USP25<87> table 2. The test article passes the test if the cytotoxicity grade is ≤2

| Grade | Reactivity | Conditions of all cultures |
|---|---|---|
| 0 | None | Discrete intracytoplasmic granules; no cell lysis |
| 1 | Slight | No more than 20% of the cells are round, loosely attached, and without intracytoplasmic granules; occasional lysed cells are present |
| 2 | Mild | No more than 50% of the cells are round and devoid of intracytoplasmic granules; no extensive cell lysis and empty areas between cells. |
| 3 | Moderate | No more than 70% of the cell layers contain rounded cells or are lysed |
| 4 | Severe | Nearly complete destruction of the cell layers. |

Results and Conclusion

No cytotoxicity was seen for any of the samples, that is all cells were healthy without any sign of toxicity. An example of a result scheme is shown in Table 5.

TABLE 5

Observed cytotoxicity from sample extracts. The tox grade score was assigned according to Table 4.

| Sample# | | Tox grade | |
|---|---|---|---|
| | | undiluted | 1 + 3 |
| 1 | 6% PVP C-15, 0.9% NaCl | 0 | 0 |
| 2 | 6% PEG 2000, 0.9% NaCl | 0 | 0 |
| Pos. control | Latex | 4 | — |
| Neg. control | Culture-medium | 0 | 0 |

FIGURE LEGENDS

FIG. 1. pH after storage of swelling media at 23° C. pH is measured at:

A: Before st.; B; After st.; C: 2 weeks; D: 3 months; E: 6 months; F: 9 months; G: 12 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 2:
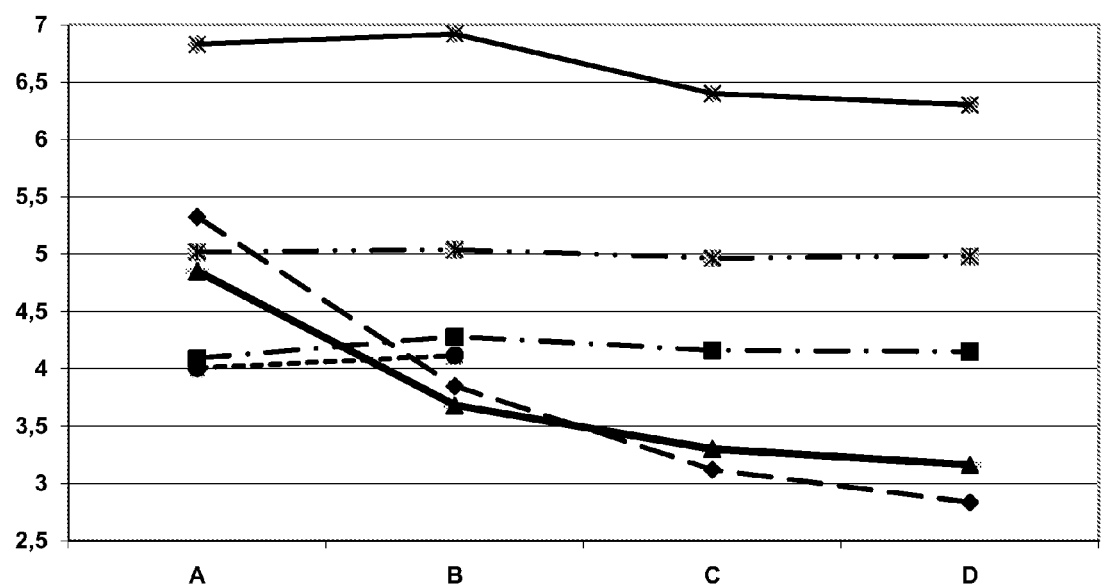

FIG. 2. pH after storage of swelling media at 40° C. pH is measured at:
A: Before st.; B; After st.; C: 6 months; D: 12 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 3:
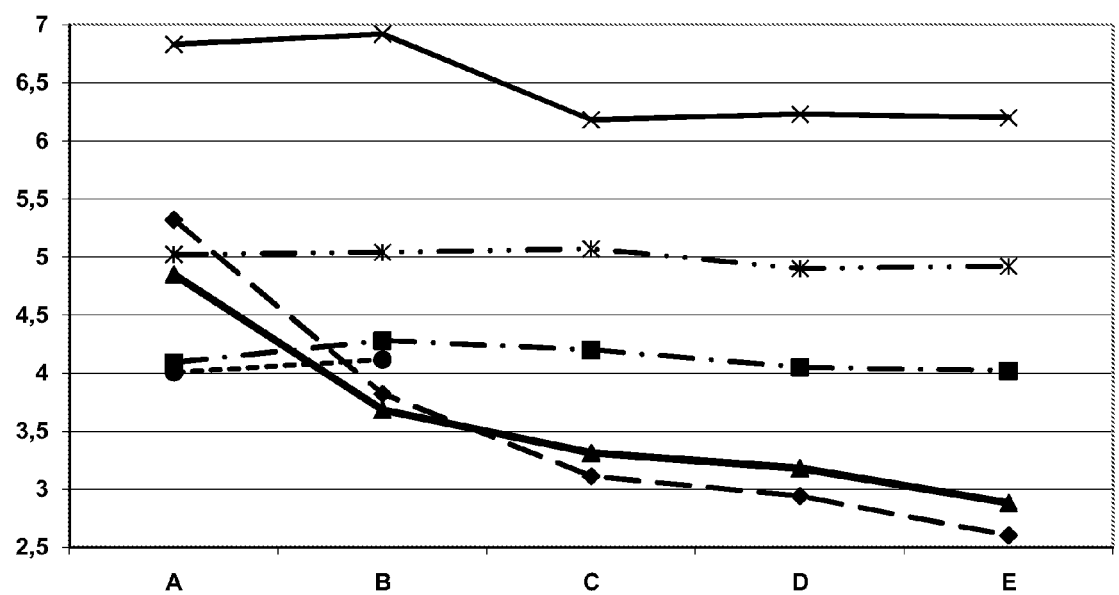

FIG. 3. pH after storage of swelling media at 50° C. pH is measured at: A: Before st.; B: After st.; C: 3 months; D: 6 months; E: 12 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 4:
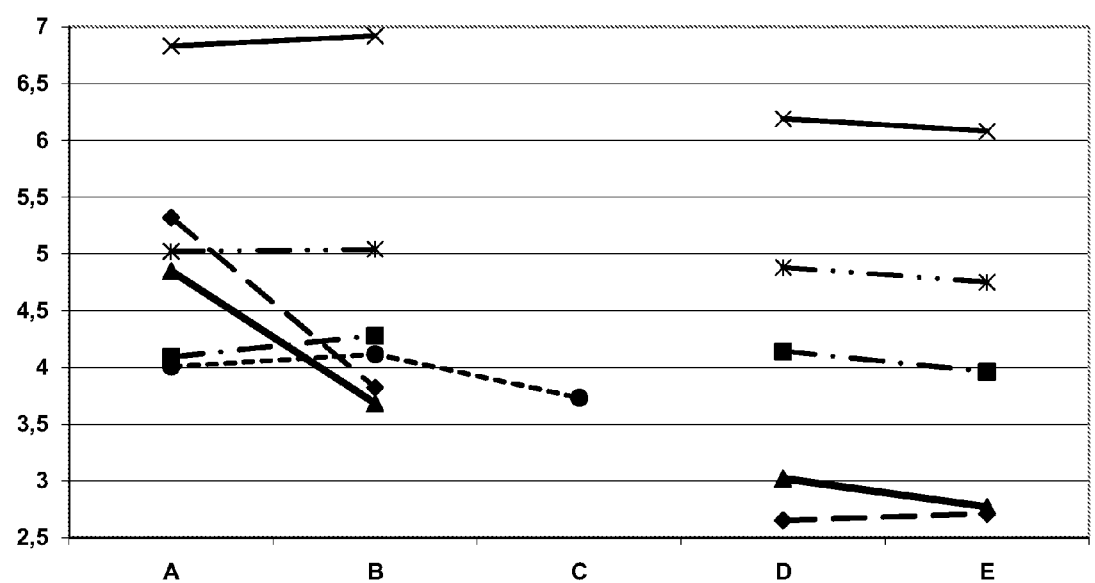

FIG. 4. pH after storage of swelling media at 60° C. pH is measured at: A: Before st.; B: After st.; C: 2 weeks; D: 3 months; D: 6 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 5:
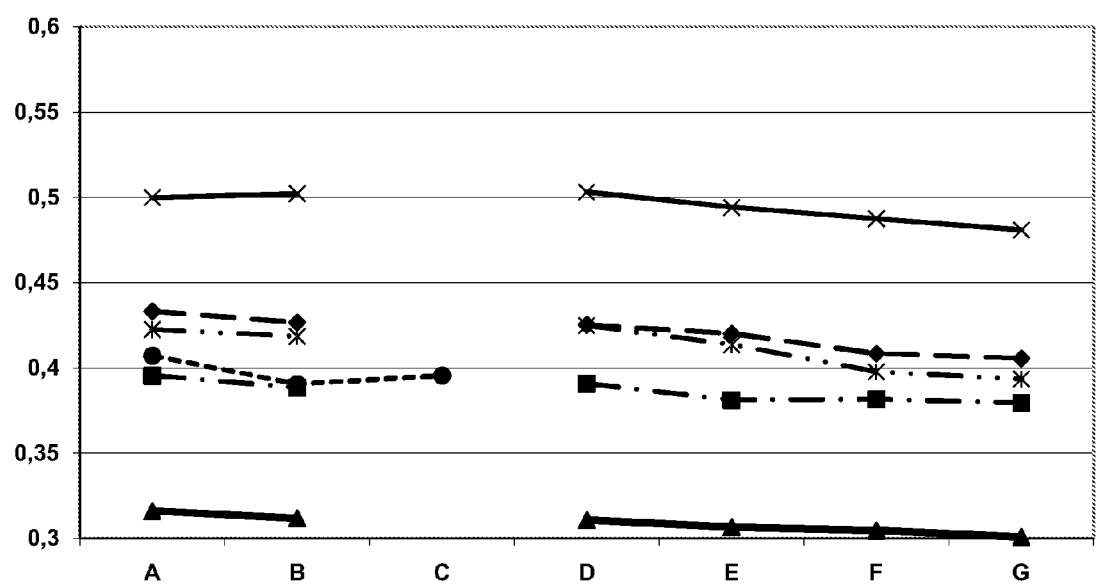

FIG. 5. Osmolality after storage of swelling media at 23° C. Osmolality (Osmol/kg) is measured at A: Before st.; B: After st.; C: 2 weeks; D: 3 months; E: 6 months; F: 9 months; G: 12 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 6:
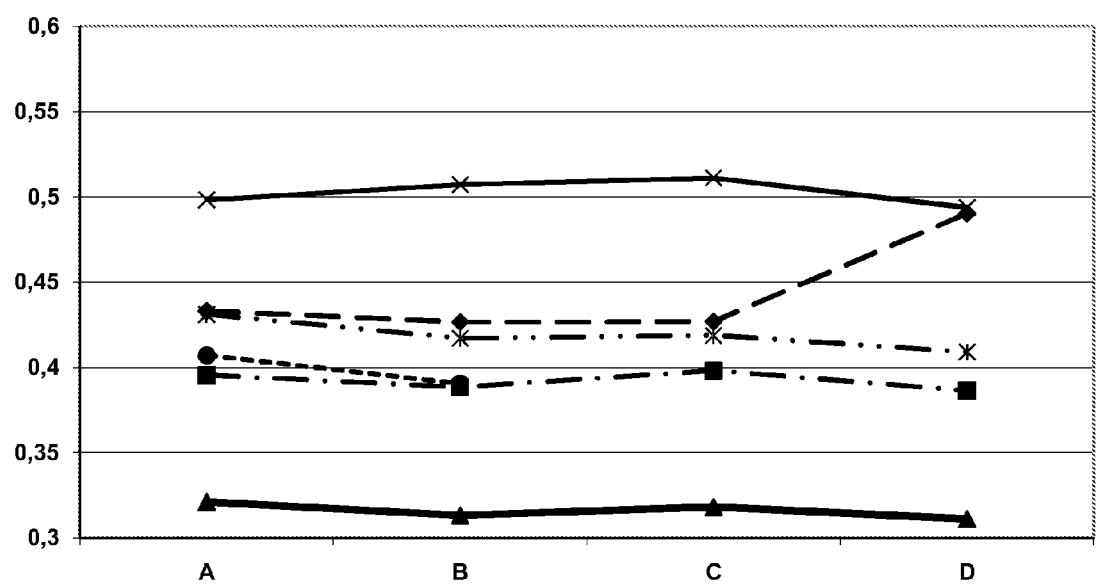

FIG. 6. Osmolality after storage of swelling media at 40° C. Osmolality (Osmol/kg) is measured at A: Before st.; B: After st.; C: 6 months; D: 12 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 7:
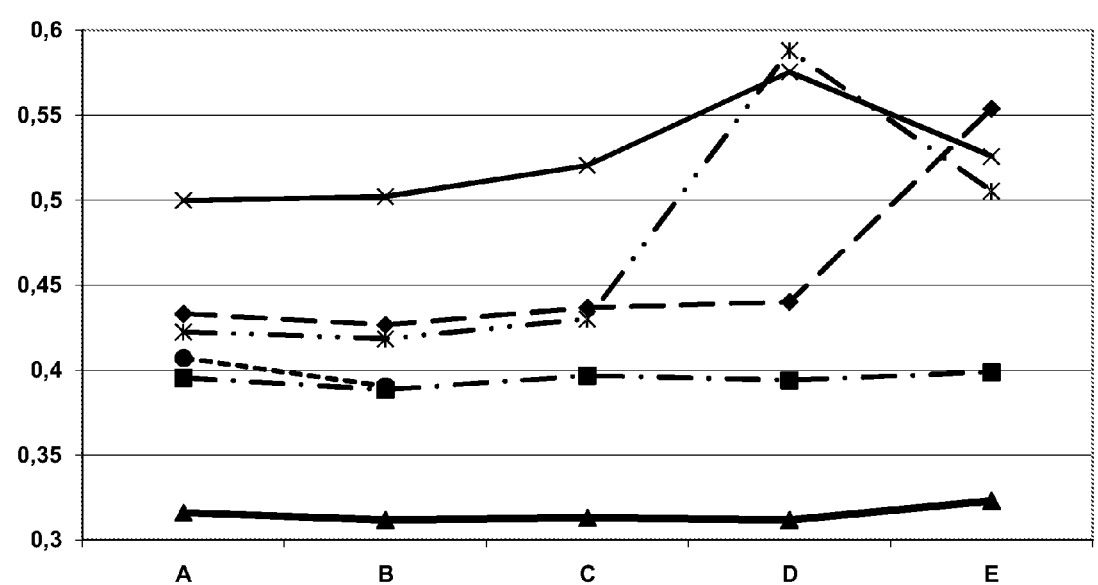

FIG. 7. Osmolality after storage of swelling media at 50° C. Osmolality (Osmol/kg) is measured at A: Before st.; B: After st.; C: 3 months; D: 6 months; E: 12 months. Measured is ▲ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 8:
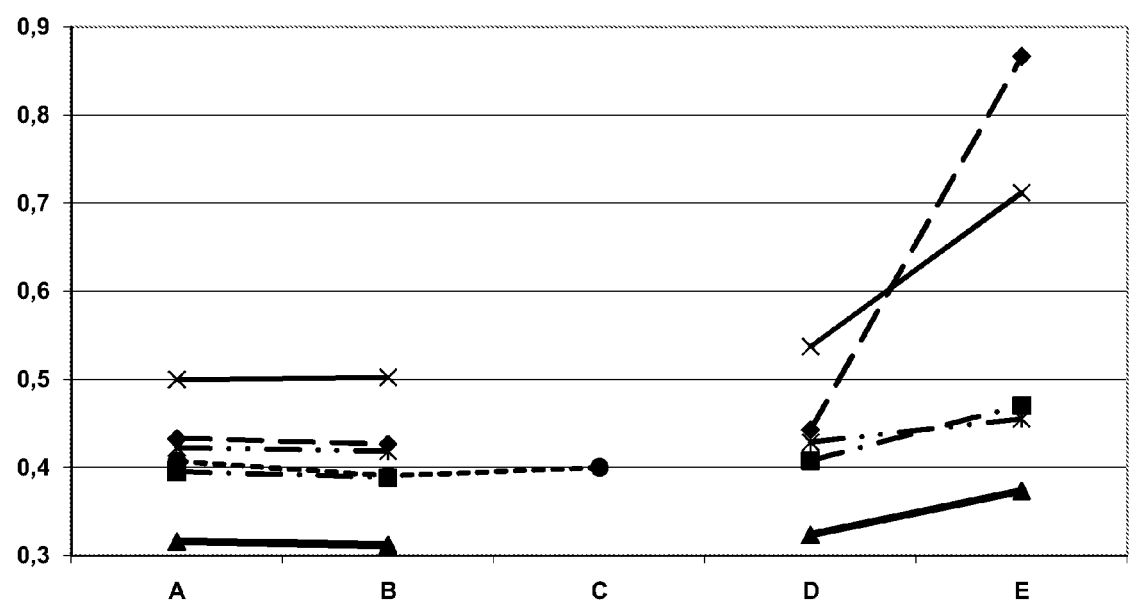

FIG. 8. Osmolality after storage of swelling media at 60° C. Osmolality (Osmol/kg) is measured at A: Before st.; B: After st.; C: 2 weeks; D: 3 months; E: 6 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 9:
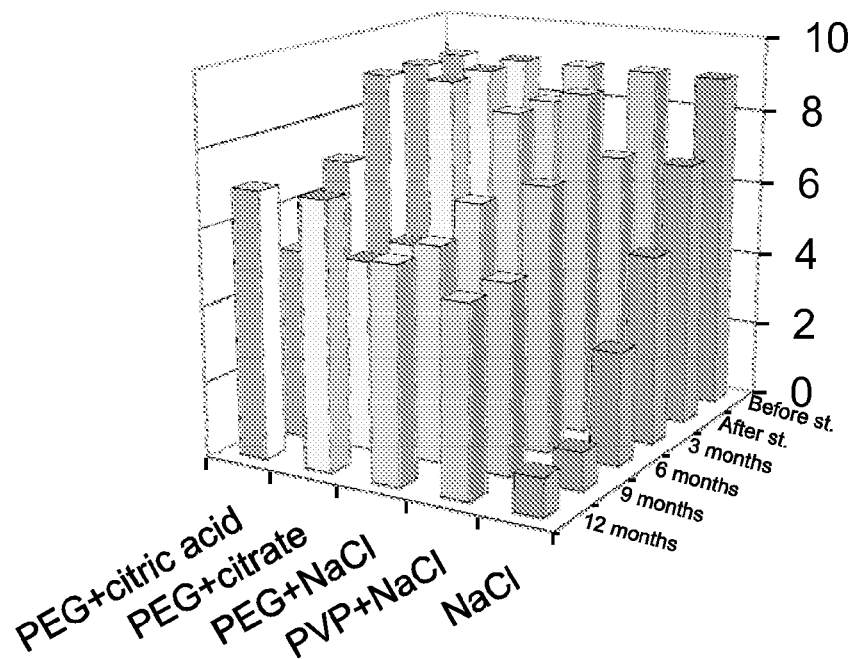

FIG. 9. Dry-out time of catheters after storage at 23° C. Dry-out time (minutes) is measured at stated time-points after storage in stated media.

Figure 10:
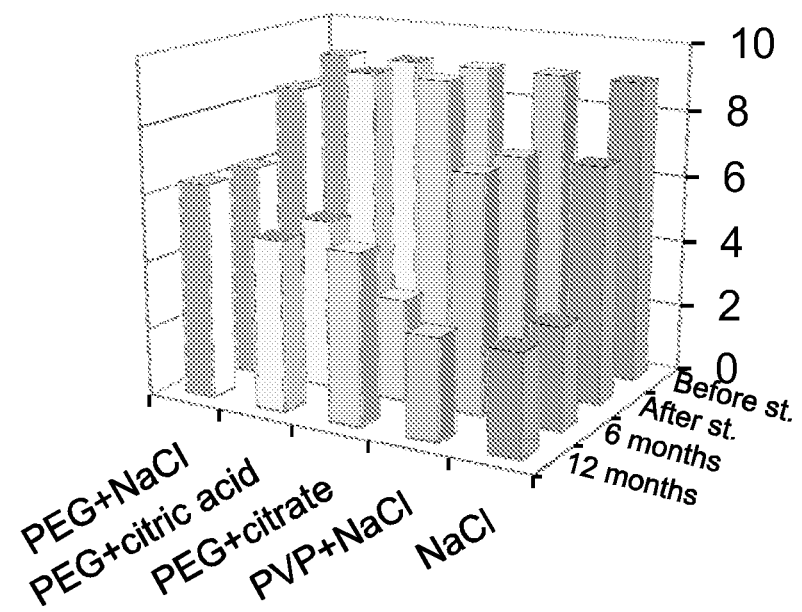

FIG. 10. Dry-out time of catheters after storage at 40° C. Dry-out time (minutes) is measured at stated time-points after storage in stated media.

Figure 11:
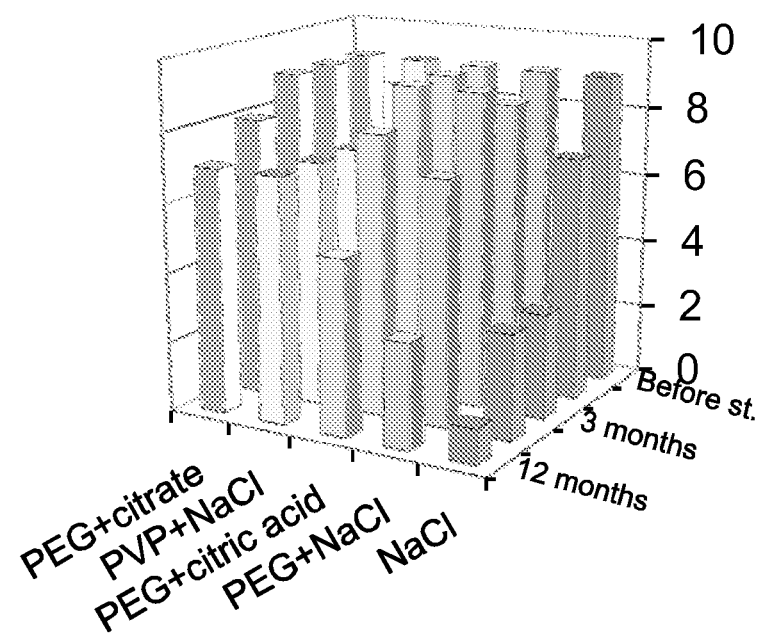

FIG. 11. Dry-out time of catheters after storage at 50° C. Dry-out time (minutes) is measured at stated time-points after storage in stated media.

Figure 12:
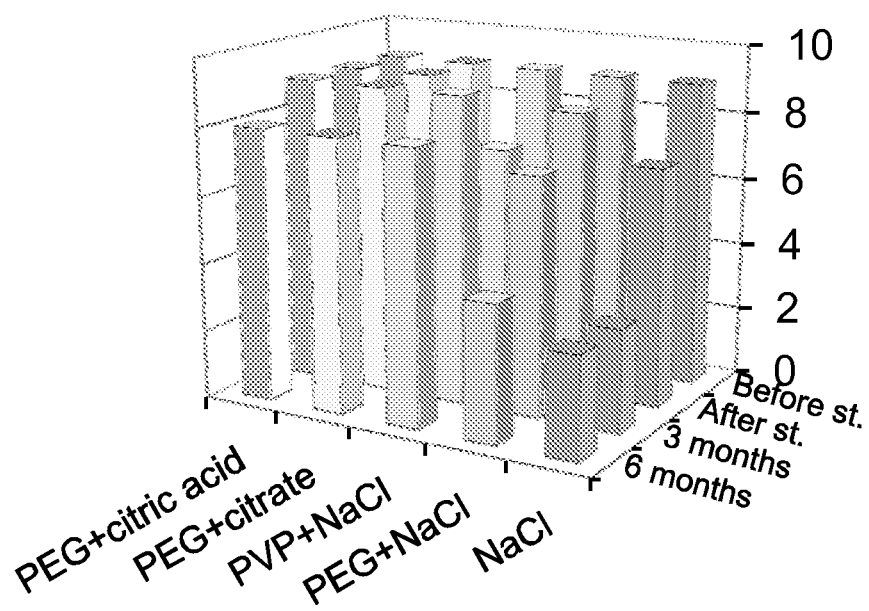

FIG. 12. Dry-out time of catheters after storage at 60° C. Dry-out time (minutes) is measured at stated time-points after storage in stated media.

Figure 13:
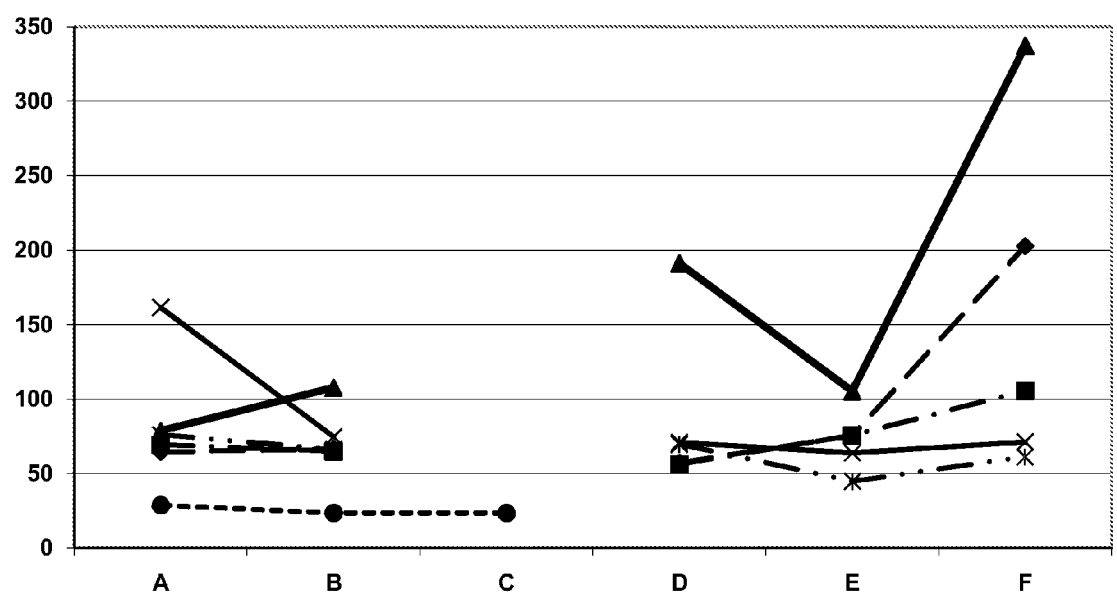

FIG. 13. Friction force of catheters after 0 minutes dry-out time after storage at 23° C. Friction force (mN) is measured at: A: Before st.; B: After st.; C: 2 weeks; D: 3 months; E: 6 months; F: 9 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 14:
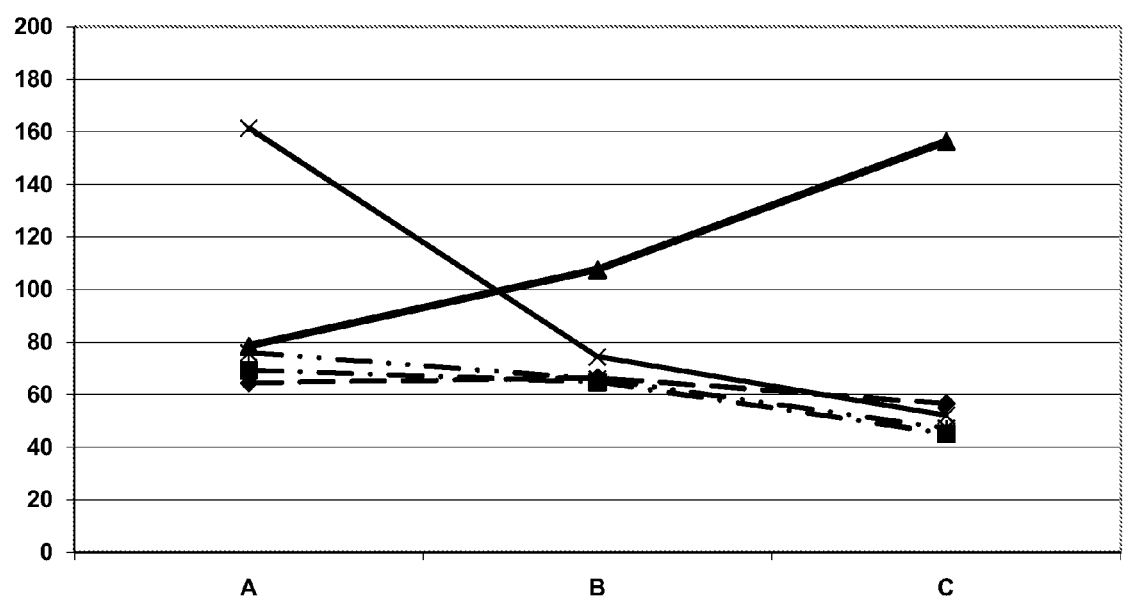

FIG. 14. Friction force of catheters after 0 minutes dry-out time after storage at 40° C. Friction force (mN) is measured at: A: Before st.; B: After st.; C: 2 weeks; D: 3 months; E: 6 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid.

Figure 15:
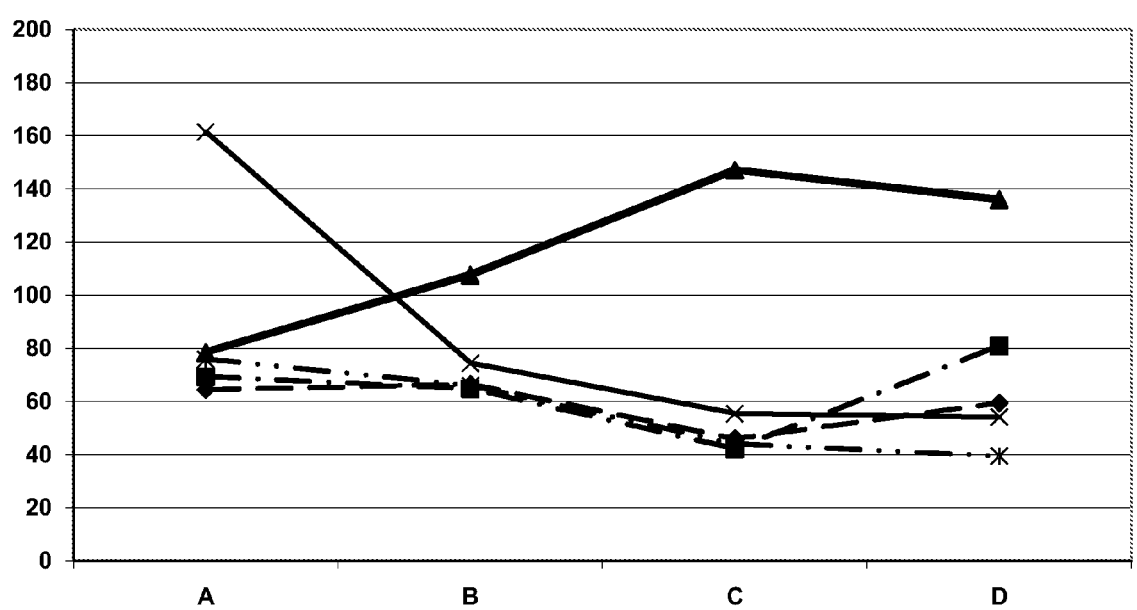

FIG. 15. Friction force of catheters after 0 minutes dry-out time after storage at 50° C. Friction force (mN) is measured at: A: Before st.; B: After st.; C: 3 months; D: 6 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid.

Figure 16:
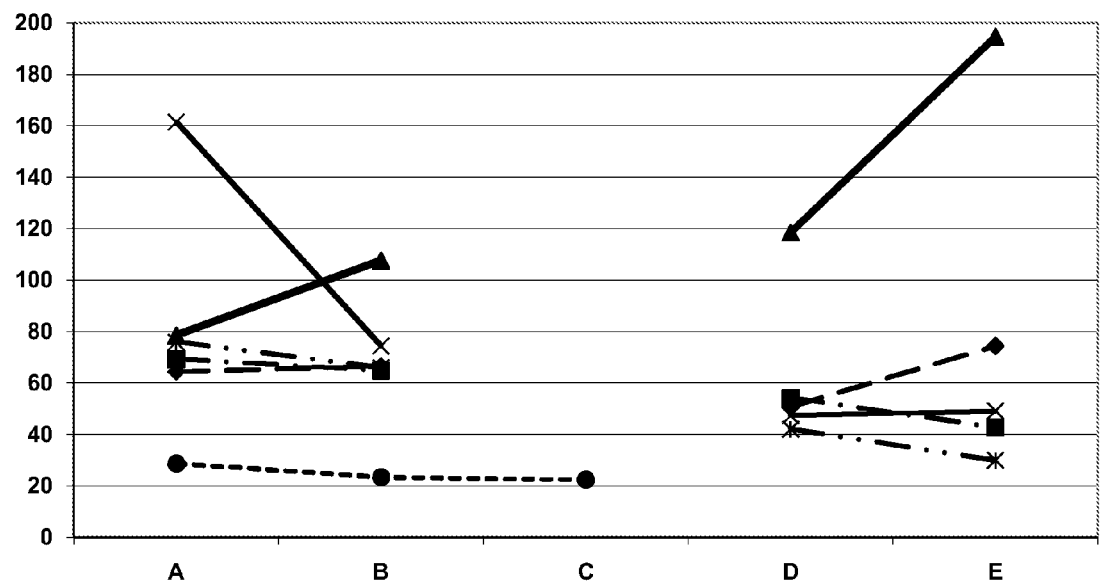

FIG. 16. Friction force of catheters after 0 minutes dry-out time after storage at 60° C. Friction force (mN) is measured at: A: Before st.; B: After st.; C: 2 weeks; D: 3 months; E: 6 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid; ● (dotted line): PEG+0.04% CA.

Figure 17:
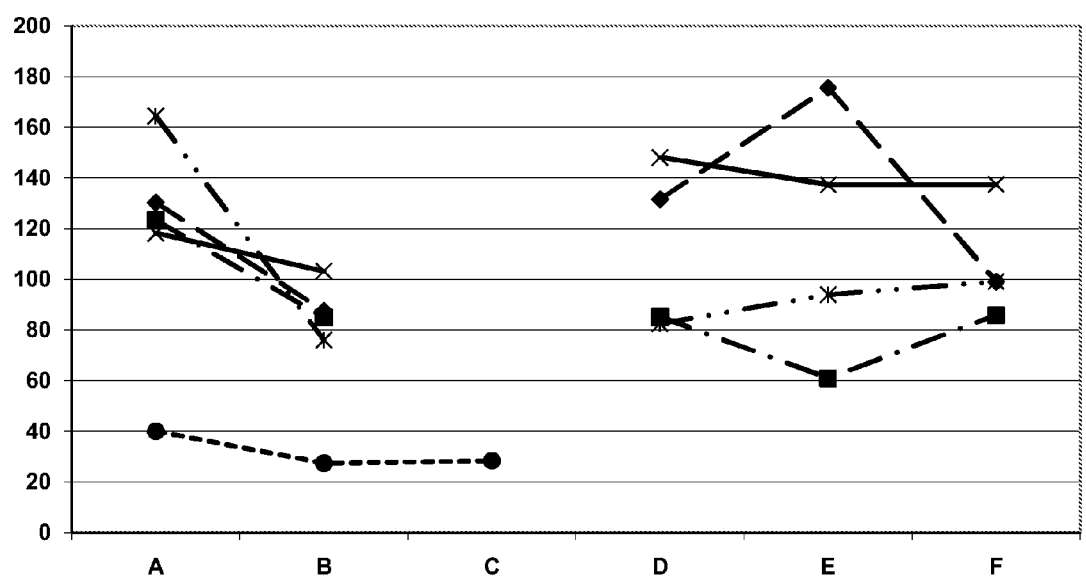

FIG. 17. Friction force of some catheters after 5 minutes dry-out time after storage at 23°. Friction force (mN) is measured at: A: Before st.; B: After st.; C: 2 weeks; D: 3 months; E: 6 months; F: 9 months. Measured is ◆ (long dotted line): PEG+NaCl; ■ (solid and one dot line): PVP+NaCl; X (solid line): PEG+citrate; ¤ (solid and two dots line): PEG+citric acid; ● (dotted line): PEG+0.04% CA.

Figure 18:
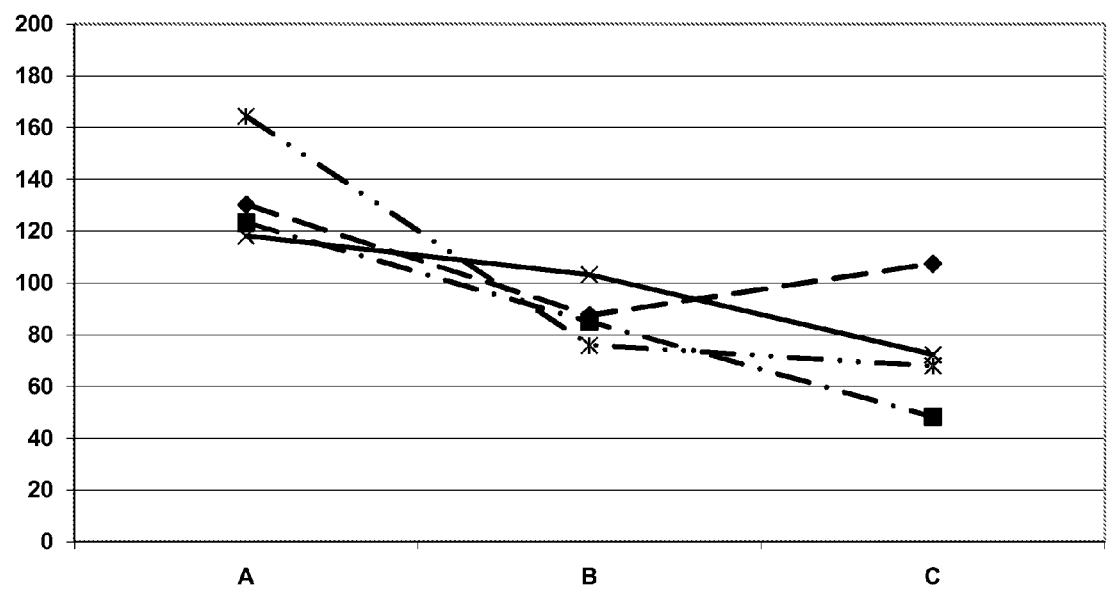
Figure 19:
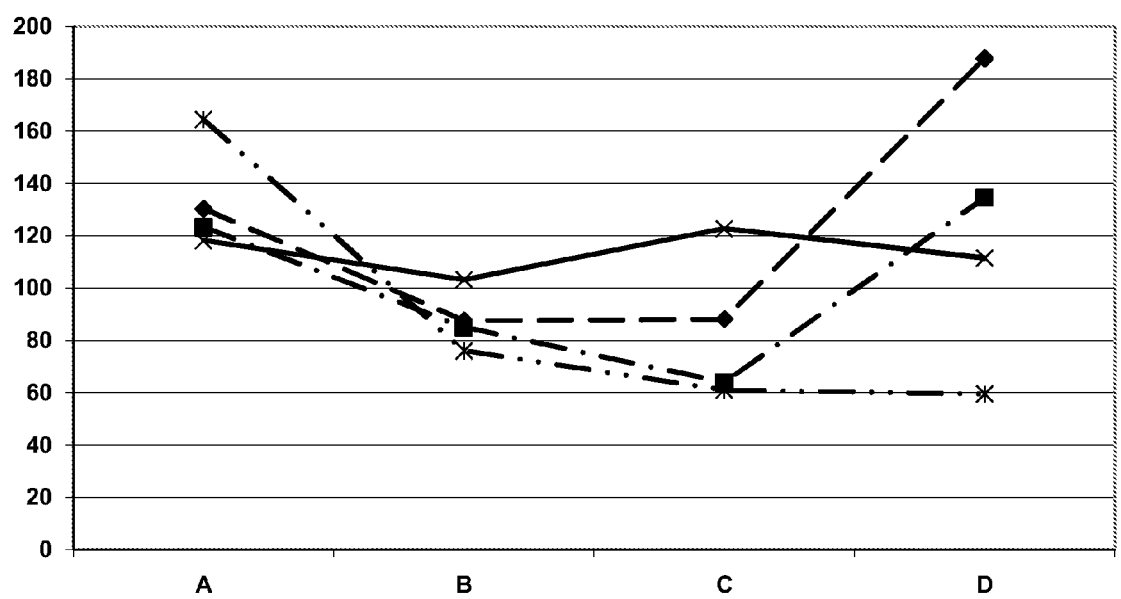
Figure 20:
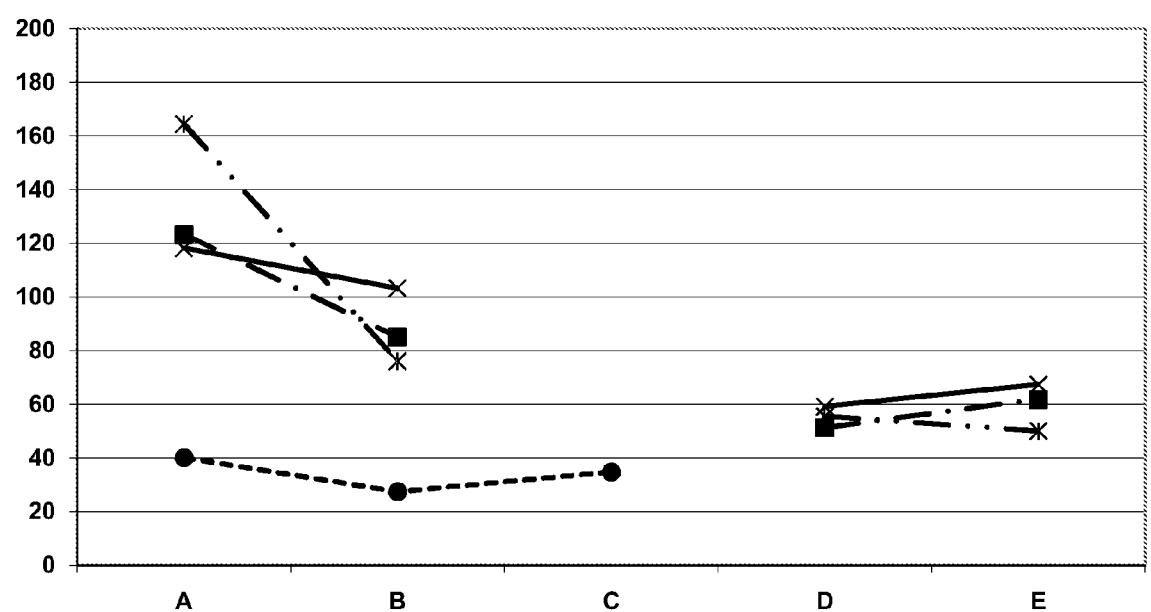

FIG. 18. Friction force of some catheters after 5 minutes dry-out time after storage at 40° C. Friction force (mN) is measured at: A: Before st.; B: After st.; C: 6 months. Measured is ◆ (long dotted line): PEG+NaCl; ■ (solid and one dot line): PVP+NaCl; X (solid line): PEG+citrate; ¤ (solid and two dots line): PEG+citric acid.

FIG. 19. Friction force of some catheters after 5 minutes dry-out time after storage at 50° C. Friction force (mN) is measured at: A: Before st.; B: After st.; C: 3 months; D: 6 months. Measured is ◆ (long dotted line): PEG+NaCl; ■ (solid and one dot line): PVP+NaCl; X (solid line): PEG+citrate; ¤ (solid and two dots line): PEG+citric acid FIG. 20. Friction force of some catheters after 5 minutes dry-out time after storage at 60° C. Friction force (mN) is measured at: A: Before st.; B: After st.; C: 2 weeks; D: 3 months; E: 6 months. Measured is ■ (solid and one dot line): PVP+NaCl; X (solid line): PEG+citrate; ¤ (solid and two dots line): PEG+citric acid; ● (dotted line): PEG+0.04% CA.

Figure 21:
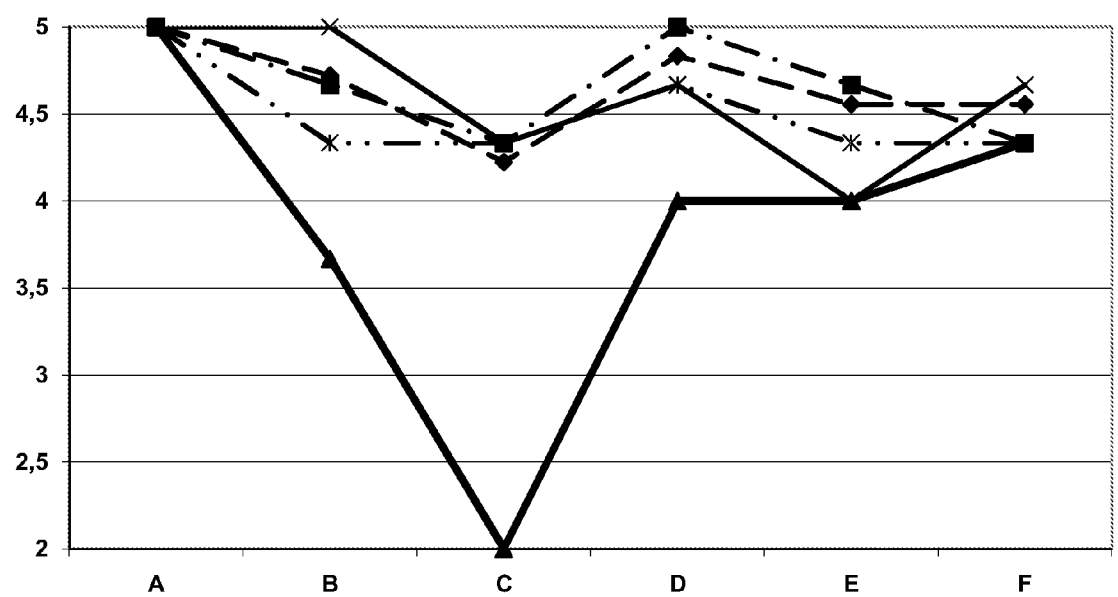

FIG. 21. Subjective slipperiness after storage at 23° C. Subjective slipperiness (0-5) is measured at: A: Before st.; B: After st.; C: 3 months; D: 6 months; E: 9 months; F: 12 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid.

Figure 22:
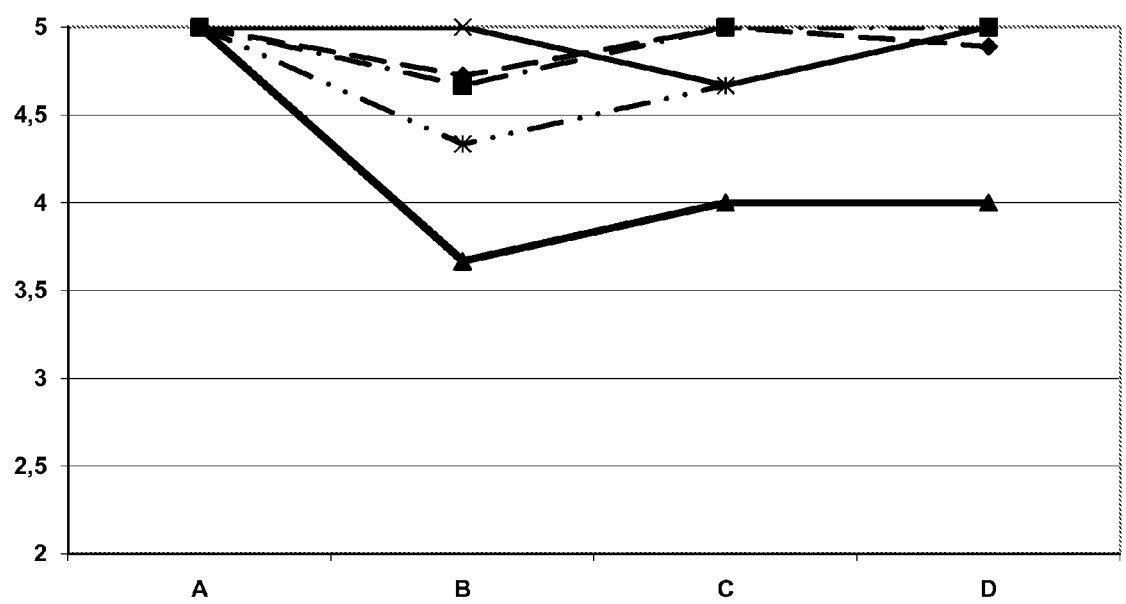

FIG. 22. Subjective slipperiness after storage at 40° C. Subjective slipperiness (0-5) is measured at: A: Before st.; B: After st.; C: 6 months; D: 12 months. Measured is ◆ (long dotted line): PEG+NaCl; ■ (solid and one dot line): PVP+NaCl; ▲ (solid line): NaCl; X (solid line): PEG+citrate; ¤ (solid and two dots line): PEG+citric acid.

Figure 23:
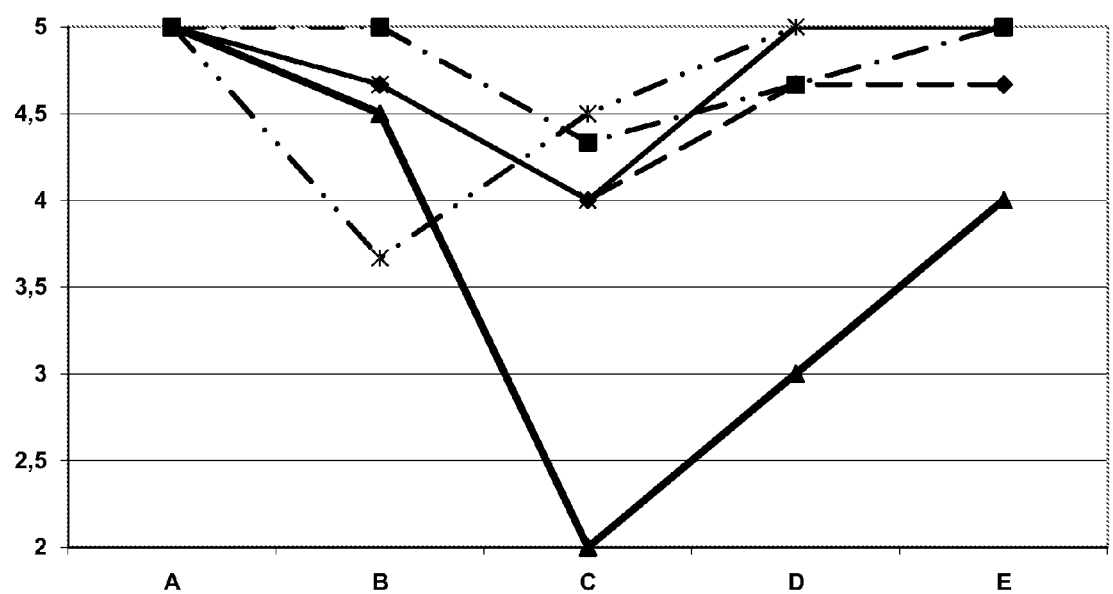

FIG. 23. Subjective slipperiness after storage at 50° C. Subjective slipperiness (0-5) is measured at: A: Before st.; B: After st.; C: 3 months; D: 6 months; E: 12 months. Measured is ◆ (long dotted line): PEG+NaCl; ■ (solid and one dot line):

PVP+NaCl; ▲ (solid line): NaCl; X (solid line): PEG+citrate; ¤ (solid and two dots line): PEG+citric acid.

Figure 24:
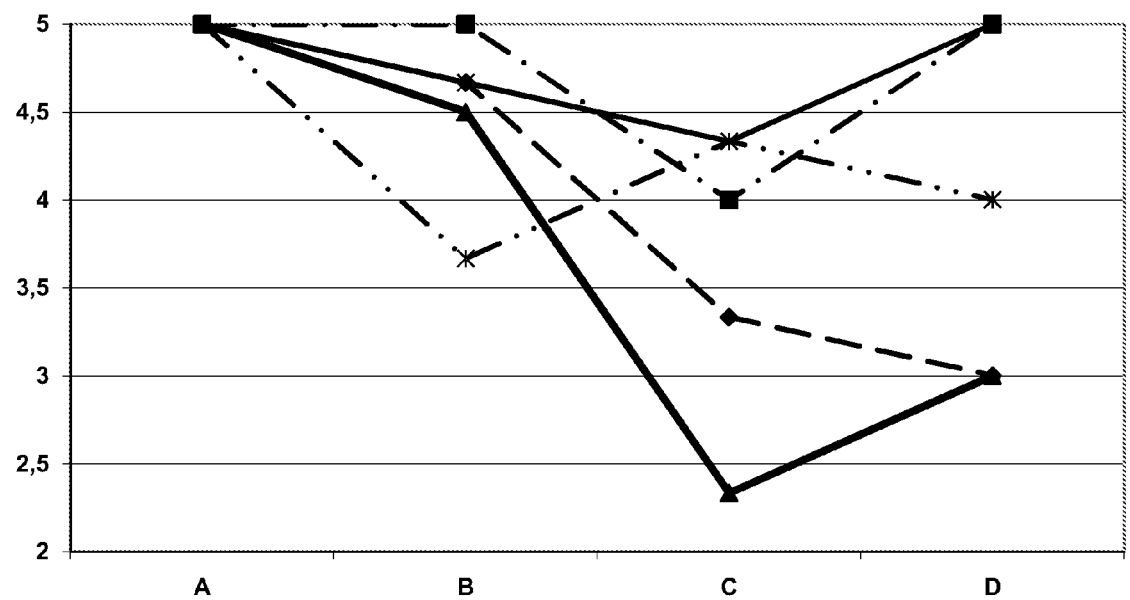

FIG. 24. Subjective slipperiness after storage at 60° C. Subjective slipperiness (0-5) is measured at: A: Before st.; B: After st.; C: 3 months; D: 6 months. Measured is ♦ (long dotted line): PEG+NaCl; ■ (solid and one dot line): PVP+NaCl; ▲ (solid line): NaCl; X (solid line): PEG+citrate; ¤ (solid and two dots line): PEG+citric acid.

Figure 25:
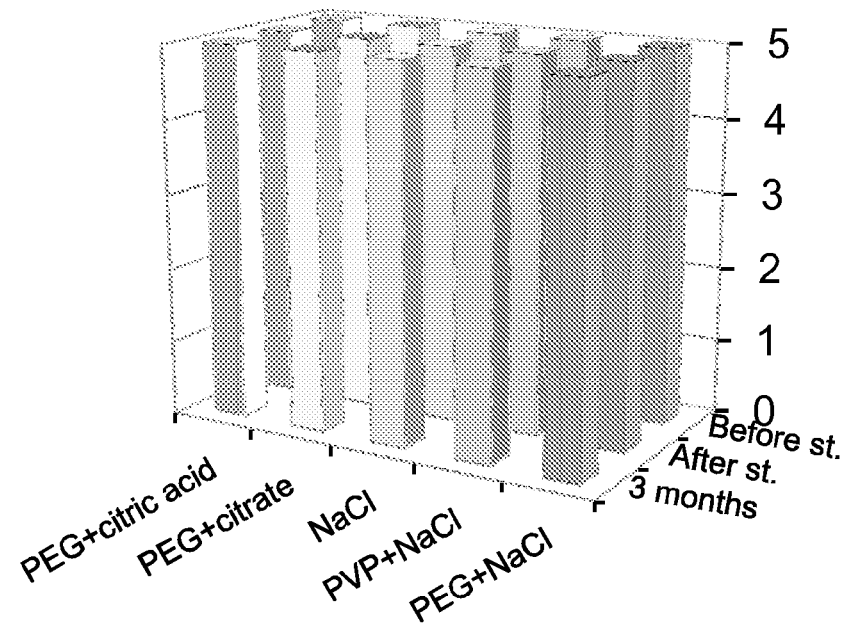

FIG. 25. Subjective coating stability after storage at 23° C. Coating stability (scale from 0-5) is measured at stated timepoints after storage in stated media.

Figure 26:
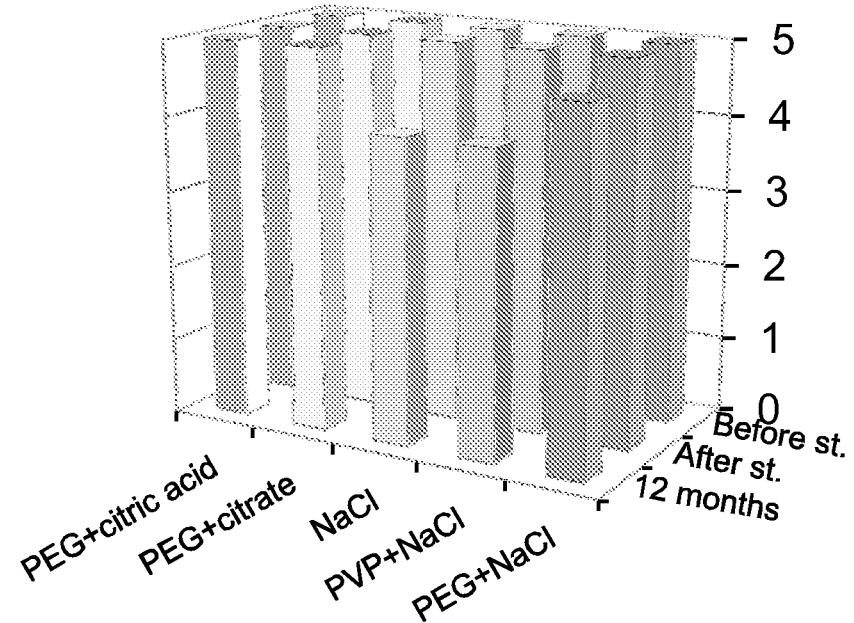

FIG. 26. Subjective coating stability after storage at 40° C. Coating stability (scale from 0-5) is measured at stated timepoints after storage in stated media.

Figure 27:
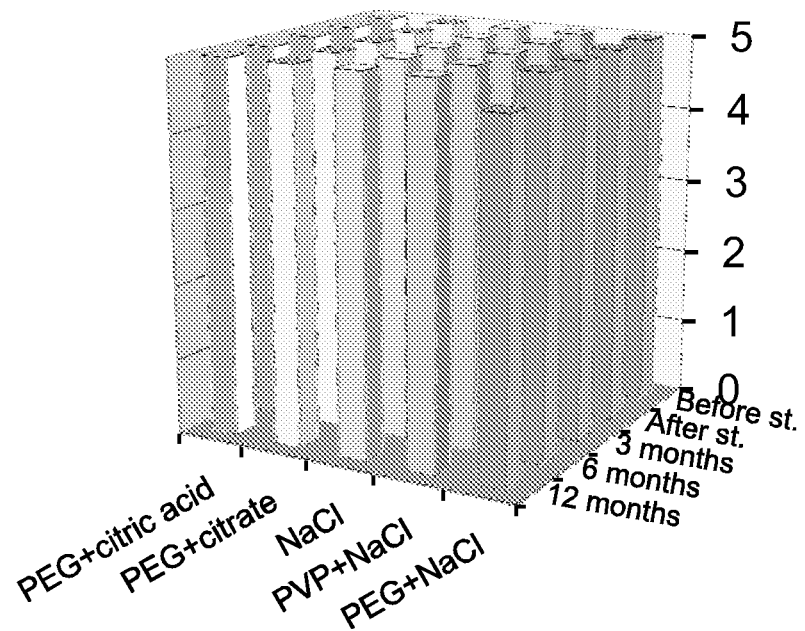

FIG. 27. Subjective coating stability after storage at 50° C. Coating stability (scale from 0-5) is measured at stated timepoints after storage in stated media.

Figure 28:
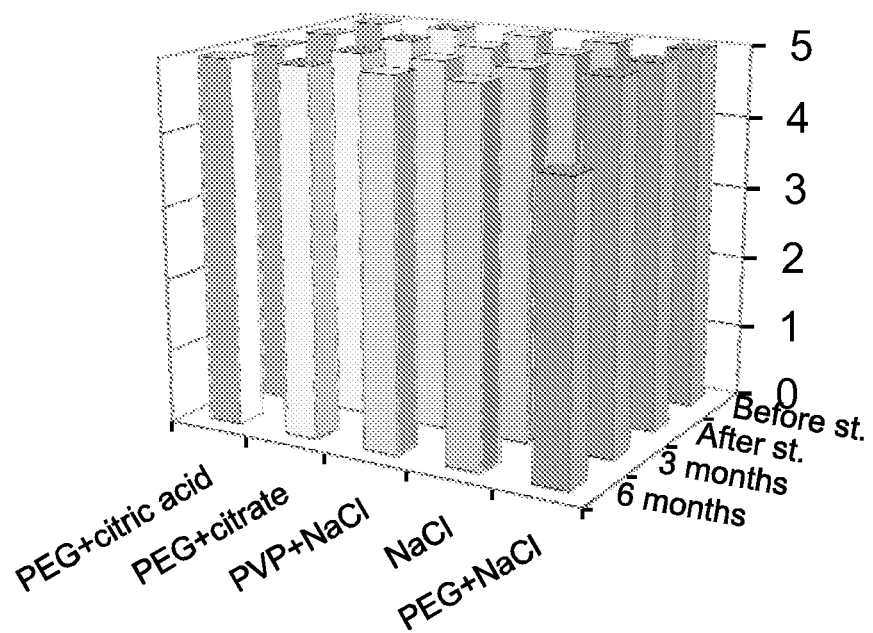

FIG. 28. Subjective coating stability after storage at 60° C. Coating stability (scale from 0-5) is measured at stated timepoints after storage in stated media.

FIG. 29. Scatter diagram of coating dry-out time versus pH across storage temperatures and storage times. Dry-out time (minutes) is plotted against varying pH. $R^2=0.1451$.

FIG. 30. Scatter diagram of coating friction force after 0 minutes dry-out versus pH across storage temperatures and storage times. Friction force after 0 minutes dry-out (mN) is plotted against varying pH.

Figure 31:
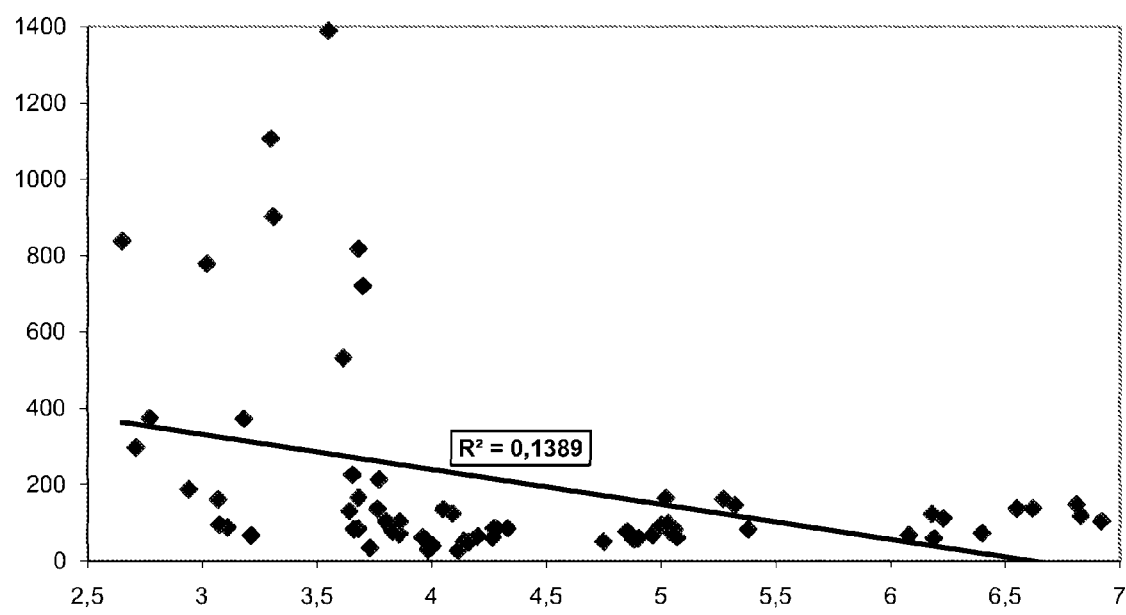

FIG. 31. Scatter diagram of coating friction force after 5 minutes dry-out versus pH across storage temperatures and storage times. Friction force after 5 minutes dry-out (mN) is plotted against varying pH. $R^2=0.1389$.

Figure 32:
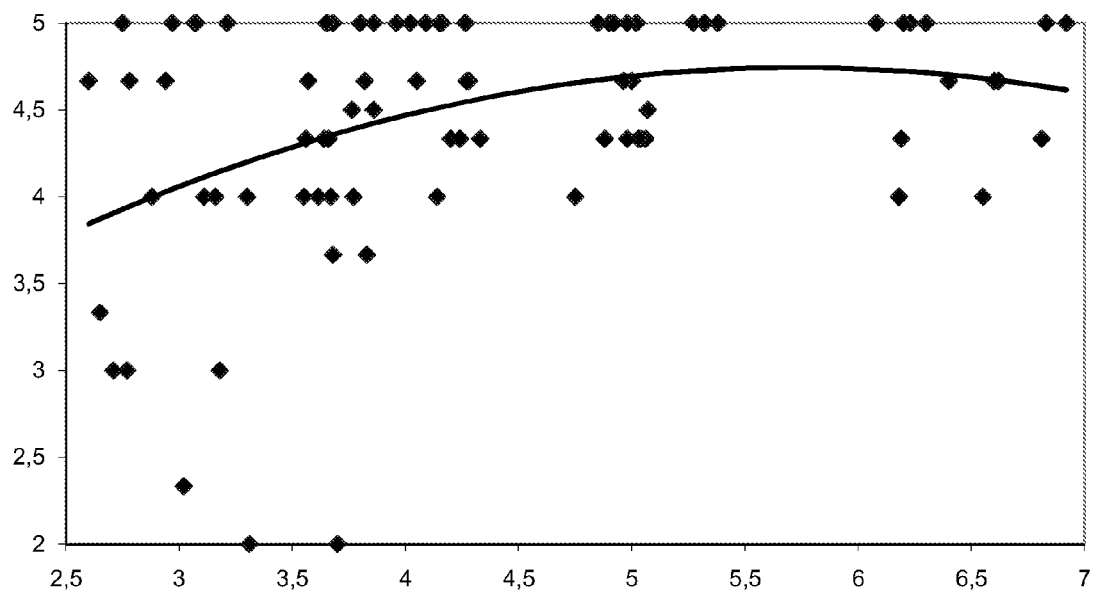
Figure 33:
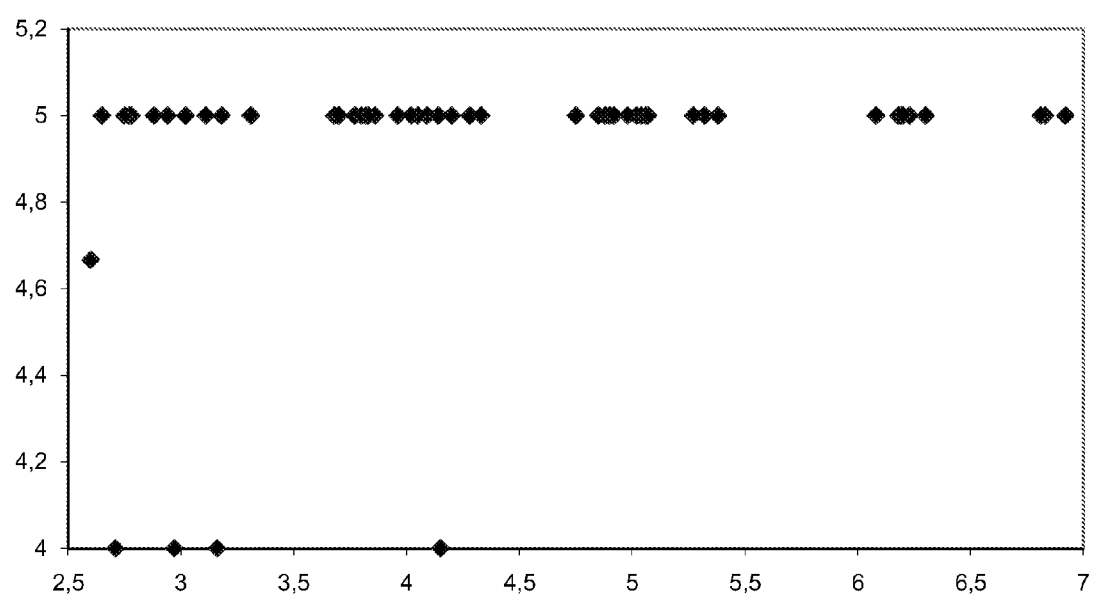

FIG. 32. Scatter diagram of subjective coating slipperiness versus pH across storage temperatures and storage times. Subjective slipperiness (0-5) is plotted against varying pH.

FIG. 33. Scatter diagram of subjective coating stability versus pH across storage temperatures and storage times. Subjective stability (0-5) is plotted against varying pH.

The invention claimed is:

1. Medical device comprising a hydrophilic coating, sterilized while in contact with a liquid having:
   a) a hydrophilic polymer; and
   b) a separate buffer selected from the group consisting of carboxylic acids, amino acids, aminosulphonic acids and inorganic acids wherein the separate buffer has at least one $pK_a$ value between 2.7 and 5.

2. Medical device according to claim 1, wherein the device is a hydrophilic coated catheter.

3. Medical device according to claim 1, wherein the hydrophilic coating is a PVP coating.

4. Medical device according to claim 1, sterilized using radiation.

5. Medical device according to claim 1, wherein the hydrophilic polymer is a hydrophilic polymer without buffer capacity.

6. Medical device according to claim 1, wherein the hydrophilic polymer is a hydrophilic polymer without buffer capacity around pH 4.

7. Medical device according to claim 1, wherein the buffer capacity is below 4 mM from pH 4 to pH 7.4.

8. A sterilized set comprising a medical device having a hydrophilic coating in contact with an aqueous liquid including:
   a) a hydrophilic polymer;
   b) a separate buffer, wherein the separate buffer has at least one $pK_a$ value between 2.7 and 5;
   wherein said set has been sterilized using irradiation while in contact with said liquid.

9. Sterilized set according to claim 8, wherein the device is a hydrophilic coated catheter.

10. Sterilized set according to claim 8, wherein the hydrophilic coating is a PVP coating.

11. Sterilized set according to claim 8, sterilized using radiation.

12. Sterilized set according to claim 8, wherein the hydrophilic polymer is a hydrophilic polymer without buffer capacity.

13. Sterilized set according to claim 8, wherein the hydrophilic polymer is a hydrophilic polymer without buffer capacity around pH 4.

14. Sterilized set according to claim 8, wherein the buffer capacity is below 4 mM from pH 4 to pH 7.4.

15. A method for sterilizing a medical device having a hydrophilic coating using radiation, said method comprising the steps bringing the medical device having such coating in contact with an aqueous liquid for wetting the hydrophilic coating, said liquid comprising a solution of a hydrophilic polymer and a separate buffer, wherein the separate buffer has at least one $pK_a$ value between 2.7 and 5, and sterilizing the device by applying a sufficient amount of radiation.

16. The method according to claim 15, wherein the device is a hydrophilic coated catheter.

17. The method according to claim 15, wherein the hydrophilic coating is a PVP coating.

18. The method according to claim 15, wherein the hydrophilic polymer is a hydrophilic polymer without buffer capacity.

19. The method according to claim 15, wherein the hydrophilic polymer is hydrophilic polymer without buffer capacity around pH 4.

20. The method according to claim 15, wherein the buffer capacity is below 4 mM from pH 4 to pH 7.4.

* * * * *